United States Patent [19]
Camps Garcia et al.

[11] Patent Number: 5,965,569
[45] Date of Patent: Oct. 12, 1999

[54] POLYCYCLIC AMINOPYRIDINE COMPOUNDS WHICH ARE ACETYLCHOLINESTERASE INHIBITORS, PROCESS FOR PREPARING THEM AND THEIR USE

[75] Inventors: Pelayo Camps Garcia; Diego Muñoz-Torrero Lopez-Ibarra; Diana Marina Görbig Romeu; Joan Contreras Lascorz; Monserrat Simon Fornell; Jordi Morral Cardoner; Rachid El Achab; Albert Badia Sancho; Josep Eladi Baños Diez; Nuria María Vivas, all of Barcelona, Spain

[73] Assignee: Medichem, S.A., Barcelona, Spain

[21] Appl. No.: 08/849,709

[22] PCT Filed: Oct. 11, 1996

[86] PCT No.: PCT/ES96/00192

§ 371 Date: Aug. 12, 1997

§ 102(e) Date: Aug. 12, 1997

[87] PCT Pub. No.: WO97/13754

PCT Pub. Date: Apr. 17, 1997

[30] Foreign Application Priority Data

Oct. 11, 1995 [ES] Spain ........................... 9501965

[51] Int. Cl.⁶ ..................... A61K 31/645; C07D 221/22
[52] U.S. Cl. ............................ 514/289; 546/63
[58] Field of Search ................ 514/289; 546/63

[56] References Cited

U.S. PATENT DOCUMENTS

| 4,695,573 | 9/1987 | Shutske et al. | 514/290 |
| 5,104,880 | 4/1992 | Kozikowski | 514/295 |
| 5,106,979 | 4/1992 | Kozikowski et al. | 546/93 |

FOREIGN PATENT DOCUMENTS

| 0268871 | 6/1988 | European Pat. Off. |
| 0278499 | 8/1988 | European Pat. Off. |
| 0311303 | 4/1989 | European Pat. Off. |
| 0319429 | 6/1989 | European Pat. Off. |
| 9313100 | 7/1993 | WIPO |

OTHER PUBLICATIONS

Wyngaarden, J.B. et al, Cecil Textbook of Medicine, 19th edition, W.B. Saunders Co., 1992, pp. 2075–2079.

Aquado, F., et al., "Synthesis and evoluation of tacrine–related compounds for the treatment of Alzheimer's desease" *European Journal of Medical Chemistry*, vol. 29, 1994, pp. 205–221.

*Primary Examiner*—Alan L. Rotman
*Assistant Examiner*—Charanjit S. Aulakh
*Attorney, Agent, or Firm*—Ladas & Parry

[57] ABSTRACT

New polycyclic aminopyridine compounds which are acetylcholinesterase inhibitors, process for preparing them and their use. The polycyclic aminopyridine compounds correspond to the formula

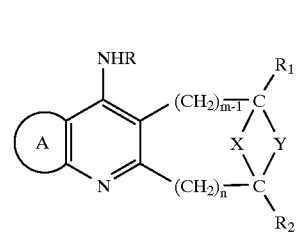

(I)

in which the various radicals have the meanings stated in the specification. The process for preparing these compounds is characterized in that ketones of general formula (II) are reacted with aminonitriles of general formula (III) and, if necessary, the compounds of formula (I) are alkylated, aralkylated or acylated, or alternatively the corresponding keto precursor is reduced. The compounds of the general formula (I) are especially suitable for the preparation of medicaments against memory disorders such as senile dementia or Alzheimer's disease.

14 Claims, No Drawings

POLYCYCLIC AMINOPYRIDINE COMPOUNDS WHICH ARE ACETYLCHOLINESTERASE INHIBITORS, PROCESS FOR PREPARING THEM AND THEIR USE

This application is a 371 of PCT/ES96/00192 which is now published as WO97/13754 on Apr. 17, 1997.

FIELD OF THE ART

The present invention relates to some new polycyclic aminopyridine compounds and to their pharmaceutically acceptable salts which are inhibitors of the enzyme acetylcholinesterase, with therapeutic benefit in the treatment of memory dysfunctions such as senile dementia or Alzheimer's disease in which medicaments capable of increasing the level of the neurotransmitter acetylcholine in the central nervous system are indicated.

PRIOR ART

Hershenson et al., J. Med. Chem. 29, 1125–1130 (1986), reported that the acetylcholine level is decreased in the brain of patients with Alzheimer's disease and have studied the benefit of physostigmine, which is an inhibitor of the enzyme acetylcholinesterase, in the treatment of the said patients.

W. K. Summers et al., Clin. Toxicol., 16, 269 (1980), reported that the known acetylcholinesterase inhibitor called tacrine, 9-amino-1,2,3,4-tetrahydroacridine, of formula

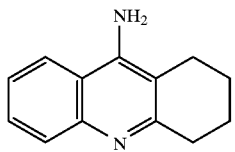

administered intravenously in combination with lecithin, proves useful in the treatment of Alzheimer's disease although it has the drawback of its high toxicity.

Subsequently, G. M. Shutske et al., J. Med. Chem. 32, 1805–1813 (1989), described 9-amino-1,2,3,4-tetrahydro-1-acridinol derivatives which also display acetylcholinesterase-inhibiting activity, and the Patents or published Patent Applications U.S. Pat. No. 4,546,104, EP-A-0268871, U.S. Pat. No. 4,735,953, U.S. Pat. No. 4,753,950, U.S. Pat. No. 4,762,841, EP-A-394950 and JP-A-03002166 describe other compounds related to the abovementioned chemical structures which also display acetylcholinesterase-inhibiting activity.

For their part, the authors of the present invention have described, in Patent Application WO 93/13100, a process for obtaining bispyridine derivatives with acetylcholinesterase-inhibiting activity.

Another known inhibitor of the abovementioned enzyme is the product called huperzine A, of formula

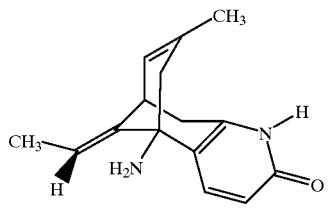

In any case, the need remains for alternative new compounds which are more effective as acetylcholinesterase inhibitors, and which permit an ever more effective and safe treatment of such serious and socially damaging diseases as Alzheimer's disease.

The authors of the present invention have discovered a group of new polycyclic aminopyridines, some of which compounds prove much more effective than tacrine in their acetylcholinesterase-inhibiting action.

SUBJECT OF THE INVENTION

The subject of the present invention is new polycyclic aminopyridine compounds and their pharmaceutically acceptable salts with high inhibitory efficacy against the enzyme acetylcholinesterase.

Another subject of the present invention is the use of the new polycyclic aminopyridine compounds and their pharmaceutically acceptable salts in the preparation of medicaments against memory disorders such as senile dementia or Alzheimer's disease, as well as the pharmaceutical compositions containing them.

Yet another subject of the present invention is a process for obtaining the abovementioned new compounds.

DESCRIPTION OF THE INVENTION

The new aminopyridine compounds which are the subject of the present invention correspond to the general formula (I):

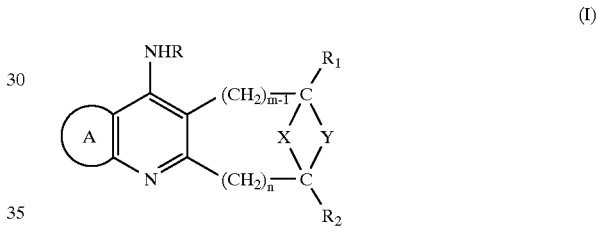

in which R can be hydrogen, alkyl, aralkyl or acyl;

$R_1$ and $R_2$ can be, independently, hydrogen, alkyl, aralkyl, alkoxy, alkoxycarbonyl, amino or amino substituted with one or two alkyl, aralkyl or acyl groups;

m and n can adopt the values 1, 2 or 3;

X and Y can be, independently, a bond between two carbons, an oxygen or sulphur atom, a group N—$R_3$ or an alkylene or alkenylene bridge containing from 1 to 5 carbon atoms and which can contain one or more substituents $R_4$. When X is an alkenylene group, the latter can be fused to a saturated or unsaturated carbocyclic or heterocyclic ring system, it being possible for the ring to be substituted with one or more groups $R_5$; for example, X can be an ortho-phenylene group;

and

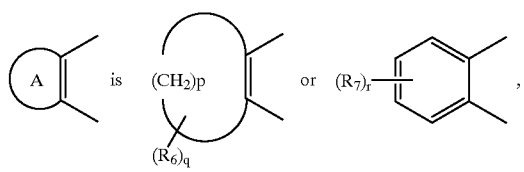

p, q and r having a value equal to or greater than one and $R_6$ and $R_7$ being substituents which can individually be hydrogen, halogen, preferably fluorine or chlorine, lower alkoxy or lower alkyl.

In the above definitions:

The term "alkyl" represents a hydrocarbon residue having one to six carbon atoms with linear, branched, substituted cyclic or cycloalkyl chains, for example methyl, ethyl, propyl, isopropyl, butyl, sec-butyl, pentyl, cyclopentyl, cyclopentylmethyl, cyclohexyl, and the like.

The term "aralkyl" means phenylalkyl or phenylalkyl substituted on the phenyl, containing from 7 to 12 carbon atoms. The term alkyl in "phenylalkyl" or "phenylalkyl substituted on the phenyl" means an alkylene group having a linear chain containing from one to four carbon atoms, for example methylene, ethylene, trimethylene or tetramethylene. The substituted phenyl in "phenylalkyl substituted on the phenyl" is a phenyl group containing one or more substituents selected from the group consisting of halogen, for example fluorine, chlorine, bromine and iodine, lower alkyl which includes alkyl groups containing from one to four carbon atoms with linear or branched chains, for example methyl, ethyl, propyl, isopropyl, butyl, sec-butyl and tert-butyl, and lower alkoxy which includes an alkoxy group having a linear or branched chain containing from one to four carbon atoms, for example methoxy, ethoxy, propoxy, isopropoxy, butoxy and sec-butoxy.

Examples of such aralkyl groups include benzyl, phenethyl, 3-phenylpropyl, 4-phenylbutyl, 2-(4-methoxyphenyl)ethyl, 2-(2-methylphenyl)ethyl, 2-(4-fluorophenyl)ethyl and 4-(4-chlorophenyl)butyl.

The term "acyl" means an alkylcarbonyl or aralkylcarbonyl group in which the alkyl and aralkyl residues can adopt the meanings defined before.

In the context of $R_1$ and $R_2$, the terms alkyl and aralkyl have the meaning given above for R. The alkoxy substituent and the alkoxy group of the alkoxycarbonyl substituent can adopt the meanings given above for the lower alkoxy group. The alkyl, aralkyl and acyl substituents of the amino group can also adopt the meanings given above in the context of R.

The group $R_3$ of N—$R_3$ can adopt the meanings defined above for R.

The groups $R_4$ attached to the alkylene or alkenylene bridge can be, independently, hydrogen, lower alkyl, alkenyl or alkylidene having one to four carbon atoms with a linear or branched chain, phenyl, phenyl substituted with one or more lower alkyl groups having one to four carbon atoms, lower alkoxy groups having one to four carbon atoms or halogen (fluorine, chlorine, bromine or iodine) groups, aralkyl as defined above in the context of R, lower alkoxy containing from one to four carbons, and hydroxyl.

The groups $R_5$ which are substituents of the ring fused to X or Y can be hydrogen, lower alkyl or lower alkoxy having one to four carbon atoms, or halogen (fluorine, chlorine, bromine and iodine).

Since the compounds of general formula (I) have at least two chiral centres, that is to say two asymmetric carbons, capable of generating optical isomerism, the present invention relates both to the racemic compounds and to all the possible enantiomers of these compounds or to the mixtures thereof in different proportions.

The pharmaceutically acceptable addition salts can be with organic or inorganic acids, such as hydrochloric, hydrobromic, sulphuric and nitric acids among inorganic acids and tartaric, succinic, maleic, fumaric and citric acids among organic acids.

The compounds of general formula (I) which are the subject of the present invention in which R is hydrogen may be prepared, in general, by reacting the ketones of general formula (II)

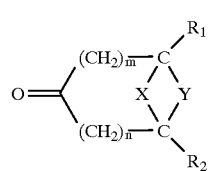

with the aminonitriles of general formula (III)

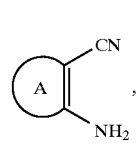

in which general formulae (II) and (III) A, $R_1$, $R_2$, X, Y, m and n have the meanings defined above, in the presence of a Lewis acid as catalyst, or of a dehydrating agent, in an appropriate solvent. The said reaction leads directly to the compounds of general formula (I) in which R is hydrogen, which may be purified by means of conventional procedures such as, for example, column chromatography, selective dissolution with different solvents or crystallization, either in the form of free bases or in the form of their addition salts with organic or inorganic acids.

In the ketones of general formula (II), it is necessary for at least one of the two indices m and n to be equal to or greater than one, that is to say it proves essential for there to be at least one methylene group in the alpha position with respect to the keto function.

The Lewis acid used as catalyst in the condensation of the ketones (II) with the aminonitriles (III) can be, inter alia, aluminium trichloride, zinc dichloride, titanium tetrachloride, and the like, all of these in anhydrous form.

As reaction solvent, aprotic solvents are used, for example nitrobenzene, 1,2-dichloroethane, dichloromethane and dimethylformamide, inter alia. The reaction is performed at temperatures of between 0 and 150° C., with reaction times which vary between 1 and 48 hours, depending on the type of catalyst and on the solvents used.

The compounds of general formula (I) in which R is other than hydrogen may be obtained by alkylation, aralkylation or acylation of the compounds of general structure (I) in which R is hydrogen, according to methods known by the expert, for example the ones described in Patent U.S. Pat. No. 4,753,950 and in the published Patent Application JP-A-03002166.

Some compounds (I) in which X or Y is an alkylene group substituted with a hydroxyl group in the endo position, for example X=CH$_2$—CH(endo—OH)—CH$_2$—, may be obtained more conveniently from the corresponding precursor compounds in which X or Y is an alkylene group substituted with an oxo group in the appropriate position, for example X=CH$_2$—CO—CH$_2$—, by reduction with appropriate reducing agents such as complex metal hydrides, for example sodium borohydride or lithium aluminium hydride, hydrogenation in the presence of a catalyst, metals in a protic medium, for example sodium in ethanol, and the like.

All the possible enantiomers of the compounds of general formula (I) may be obtained by means of conventional techniques well known to the expert, for example by means of selective or fractional crystallization of their diastereoisomeric salts with optically active organic acids, by chromatographic methods, by means of enantioseletive synthesis, and the like.

The reactions of formation of the pharmaceutically acceptable salts of the compounds of general formula (I) are performed by conventional methods, by reacting the basic organic compound with an organic or inorganic acid in a suitable solvent such as water, alcohols, for example methanol, ethanol, isopropanol, and the like, or ethers such as diethyl ether, tetrahydrofuran, dioxane, and the like.

Preference is given, as the subject of the present invention, to the compounds which, among those encompassed by the general formula (I), correspond to the general formula

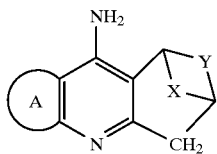

in which A, X and Y have the meanings already stated for the general formula (I).

The said compounds may be obtained by reacting the ketones which, among those encompassed by the general formula (II), correspond to the general formula

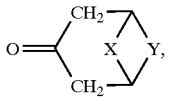

in which X and Y have the meanings already given, with the aminonitriles of general formula (III), in the manner already explained for obtaining the compounds of general formula (I).

Among the starting ketones (II) for obtaining the compounds which are the subject of the invention, there may be mentioned by way of special cases the ones shown in Table 1.

Examples of starting ketones (II).

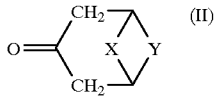

| Ref. | X | Y |
|---|---|---|
| IIa | —CH₂— | —CH₂—CH=CH— |
| IIb | —CH₂— | —CH₂—C(CH₃)=CH— |
| IIc | —CH₂— | —CH₂—C(C₂H₅)=CH— |
| IId | —CH₂— | —CH₂—C(n-C₃H₇)=CH— |
| IIe | —CH₂— | —CH₂—C(n-C₄H₉)=CH— |
| IIf | —CH₂— | —CH₂—C(C₆H₅)=CH— |
| IIg | —CH₂— | —CH₂—CH₂—CH₂— |
| IIh | —CH₂— | —CH₂—CH(exo-OH)—CH₂— |
| IIi | —C(CH₃) (syn-OCH₃)— | —CH₂—C(CH₃)=CH— |
| IIj | —C(CH₃) (anti-OCH₃)— | —CH₂—C(CH₃)=CH— |
| IIk | —CO— | —CH₂—C(CH₃)=CH— |
| IIl | (E) —C(=CH—CH₃)— | —CH₂—C(CH₃)=CH— |
| IIm | (Z) —C(=CH—CH₃)— | —CH₂—C(CH₃)=CH— |
| IIn | o-phenylene | —CH₂—C(CH₃)=CH— |
| IIo | o-phenylene | —CH₂—CH₂—CH₂— |

Some of the ketones (II) used as starting materials in the preparation of the compounds (I) are compounds which have been described before, and they may consequently be prepared in accordance with the said previous descriptions. Thus, IIa has been described by J. G. Henkel et al., J. Org. Chem. 48, 3858–3859 (1983); IIb by K. Kimoto et al., Bull. Chem. Soc. Jpn. 45, 3698–3702 (1972); IIf by H. Quast et al., Liebigs Ann., 725–738 (1995); IIg by T. Momose et al., Chem. Pharm. Bull. 26, 288–295 (1978), IIh by R. S. Henry et al., J. Chem. Soc., Perkin Trans. 2, 1549–1553 (1976); and IIo by R. Bishop, Aust. J. Chem. 37, 319–325 (1984).

The ketones IIc, IId, IIe, IIi, IIj and IIk, as well as other ketones related to these compounds, may be prepared by means of a process which consists of the reaction sequence in the following scheme:

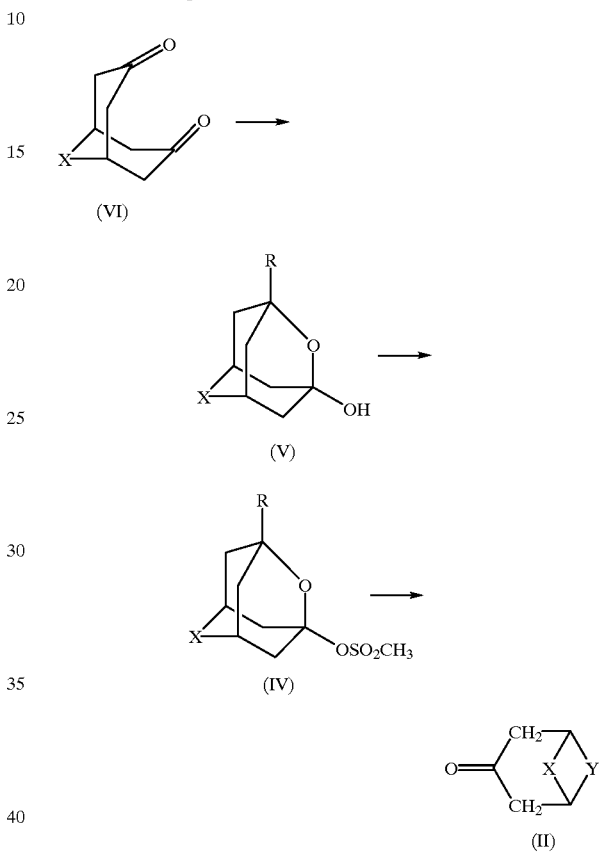

The diketones (VI), in which X has the meaning already given, are reacted with organometallic (organomagnesium or organolithium) reagents to give rise to the oxaadamantanols (V) which, on reaction with methanesulphonyl chloride, give rise to the corresponding methanesulphonates (IV). The latter, on treatment with silica gel, are converted to the corresponding ketones (II).

The ketones IIl and IIm, as well as other ketones related to these compounds, may be obtained in accordance with the reaction sequence in the following scheme:

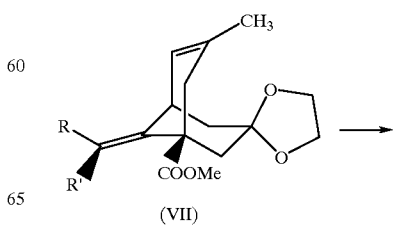

-continued

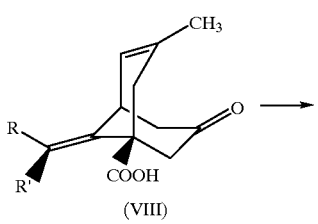

(VIII)

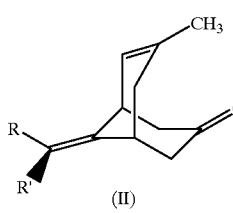

(II)

that is to say by means of hydrolysis of the acetal esters (VII), the preparation of which may be performed in accordance with the method described by A. P. Kozikowski et al., Heterocycles 39, 101–116 (1994), and decarboxylation of the corresponding keto acids (VIII).

The ketone IIn was prepared from the ketone acetal IX, described by P. Camps et al., Tetrahedron Lett. 35, 3187–3190 (1994), by reaction with methyllithium followed by dehydration and-hydrolysis of the alcohol X formed, in accordance with the following scheme:

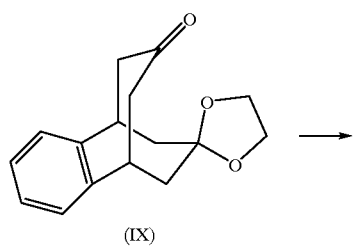

(IX)

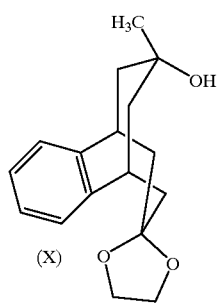

(X)

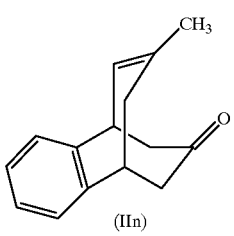

(IIn)

Ketones related to IIn may be prepared in a similar manner.

In general, the starting ketones (II) may be prepared by means of any one of the methods described, introducing variations which are obvious to the expert in accordance with the substituents which are desired.

Among the starting aminonitriles (III) for obtaining the compounds which are the subject of the invention, there may be mentioned by way of special cases the ones shown in Table 2.

TABLE 2

Examples of starting aminonitriles (III).

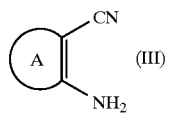

| Ref. | |
|---|---|
| IIIv | 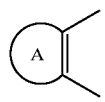 |
| IIIw | 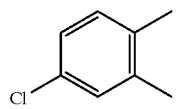 |
| IIIx | 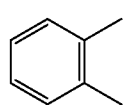 |
| IIIy | 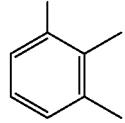 |
| IIIz | 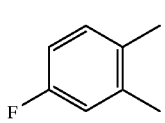 |
| | 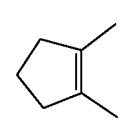 |

The aminonitriles IIIv, IIIw and IIIx may be acquired on the market. The remaining aminonitriles may be obtained in accordance with the processes described by F. Hunziker et al., Eur. J. Med. Chem.. 16, 391–398 (1981) and by H. E. Schroeder et al., J. Am. Chem. Soc. 71, 2205–2207 (1949). In general, the compounds of general formula (III) are known and may be prepared by conventional means readily accessible to the expert.

Among the compounds of general formula (I) obtained, there may be mentioned by way of special cases the ones shown in Table 3. Each compound is named using the Roman numeral I followed by two lower-case letters which correspond, in the first place to the one assigned in Table 1 to the starting ketone from which it is formed, and in the second place to the one assigned in Table 2 to the aminonitrile from which it is also formed.

TABLE 3

Examples of compounds of general formula (I).

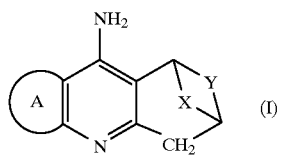

| Ref. | starting ketone (II) | starting amino-nitrile (III) | chemical name |
|---|---|---|---|
| Iaw | IIa | IIIw | 12-Amino-6,7,10,11-tetrahydro-7,11-methanocycloocta [b] quinoline |
| Ibw | IIb | IIIw | 12-Amino-6,7,10,11-tetrahydro-9-methyl-7,11-methanocycloocta [b]-quinoline |
| Ibx | IIb | IIIx | 12-Amino-1-fluoro-6,7,10,11-tertrahydro-9-methyl-7,11-methanocycloocta-[b] quinoline |
| Iby | IIb | IIIy | 12-Amino-3-fluoro-6,7,10,11-tertrahydro-9-methyl-7,11-methanocycloocta [b] quinoline |
| Ibz | IIb | IIIz | 11-Amino-2,3,5,6,9,10-hexahydro-8-methyl-6,10-methano-1H-cycloocta [e]-cyclopenta [b] pyrdine |
| Icv | IIc | IIIv | 12-Amino-3-chloro-9-ethyl-6,7,10,11-tetrahydro-7,11-methanocycloocta [b] quinoline |
| Icw | IIc | IIIw | 12-Amino-9-ethyl-6,7,10,11-tetrahydro-7,11-methanocycloocta [b]-quinoline |
| Icx | IIc | IIIx | 12-Amino-9-ethyl-1-fluoro-6,7,10,11-tetrahydro-7,11-methanocycloocta [b] quinoline |
| Icy | IIc | IIIy | 12-Amino-9-ethyl-3-fluoro-6,7,10,11-tetrahydro-7,11-methanocycloocta [b] quinoline |
| Idw | IId | IIIw | 12-Amino-6,7,10,11-tetrahydro-9-propyl-7,11-methanocycloocta [b]-quinoline |
| Iew | IIe | IIIw | 12-Amino-9-butyl-6,7,10,11-tetrahydro-7,11-methanocycloocta [b]-quinoline |
| Ifw | IIf | IIIw | 12-Amino-9-phenyl-6,7,10,11-tetrahydro-7,11-methanocycloocta [b]-quinoline |
| Igw | IIg | IIIw | 12-Amino-6,7,8,9,10,11-hexahydro-7,11-methanocycloocta [b] quinoline |
| Ihw | IIh | IIIw | 12-Amino-6,7,8,9,10,11-hexahydro-7,11-methanocycloocta [b] quinolin-9-exo-ol |
| Iiw | IIi | IIIw | syn-12-Amino-6,7,10,11-tetrahydro-9,13-dimethyl-13-methoxy-7,11-methanocycloocta [b] quinoline |
| Ijw | IIj | IIIw | anti-12-Amino-6,7,10,11-tetrahydro-9,13-dimethyl-13-methoxy-7,11-methanocycloocta [b] quinoline |
| Ikw | IIk | IIIw | 12-Amino-6,7,10,11-tetrahydro-9-methyl-7,11-methanocycloocta [b]-quinolin-13-one |
| Ilw | IIl | IIIw | 12-Amino-6,7,10,11-tetrahydro-9-methyl-7,11-[1]-(Z)propenylidenocycloocta [b] quinoline |
| Imw | IIm | IIIw | 12-Amino-6,7,10,11-tetrahydro-9-methyl-7,11-[1]-(E)propenylidenocycloocta [b] quinoline |
| Inw | IIn | IIIw | 12-Amino-6,7,10,11-tetrahydro-9-methyl-7,11-o-benzenocycloocta [b]-quinoline |
| Iow | IIo | IIIw | 12-Amino-6,7,8,9,10,11-hexahydro-7,11-o-benzenocycloocta [b] quinoline |
| Iqw | — | — | 12-Amino-6,7,8,9,10,11-hexahydro-7,11-o-benzenocycloocta [b] quinolin-9-endo-ol |
| Irw | — | — | 12-Amino-6,7,8,9,10,11-hexahydro-7,11-methanocycloocta [b] quinolin-9-endo-ol |
| Irz | — | — | 11-Amino-2,3,5,6,7,8,9,10-octahydro-6,10-methano-1H-cycloocta [e]-cyclopenta [b] pyridin-8-endo-ol |

The structural formulae of the compounds in Table 3 are as follows:

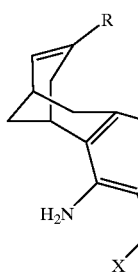

Iaw, R = X = X' = H
Ibw, R = Me, X = X' = H
Ibx, R = Me, X = F, X' = H
Iby, R = Me, X = H, X' = F
Icv, R = Et, X = H, X' = Cl
Icw, R = Et, X = X' = H
Icx, R = Et, X = F, X' = H
Icy, R = Et, X = H, X' = F
Idw, R = Pr, X = X' = H
Iew, R = Bu, X = X' = H
Ifw, R = phenyl, X = X' = H

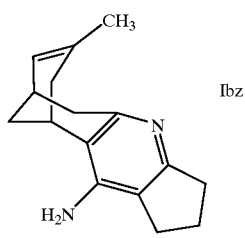

Ibz

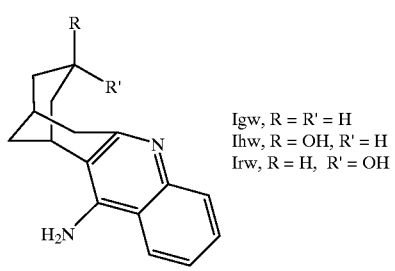

Igw, R = R' = H
Ihw, R = OH, R' = H
Irw, R = H, R' = OH

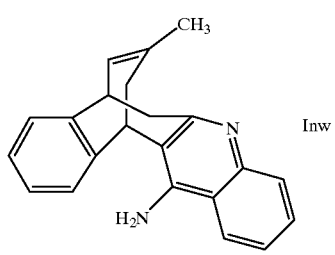

Inw

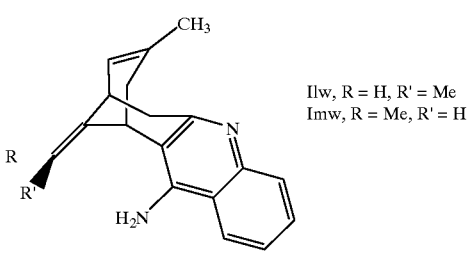

Ilw, R = H, R' = Me
Imw, R = Me, R' = H

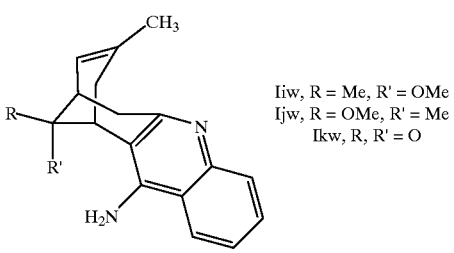

Iiw, R = Me, R' = OMe
Ijw, R = OMe, R' = Me
Ikw, R, R' = O

Iow, R = R' = H
Iqw, R = H, R' = OH

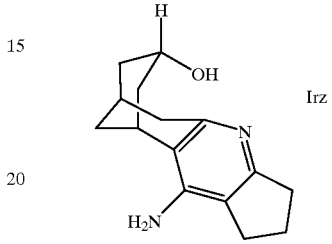

Irz

The products Iqw, Irw and Irz are not obtained by direct reaction of a ketone (II) with an aminonitrile (III), but by reduction of direct keto precursors described by the authors of the present invention in Patent Application WO 93/13100. Nonetheless, for consistency, the manner of naming them has been maintained, as if they originated from hypothetical starting ketones IIq and IIr.

The remainder of the products of general formula (I) may be obtained by reacting the ketones (II) with the aminonitriles (III) in the manner already explained.

The compounds of general formula (I) in enantiomerically pure form may be obtained by various procedures: for example by medium pressure column chromatography using 15–25 μm microcrystalline cellulose triacetate (Merck) as chiral stationary phase, as described in Examples 37 and 38.

Alternatively, some of the compounds of general formula (I) in enantiomerically pure form may be obtained via enantioselective syntheses, analogously to the preparation of the corresponding racemic compounds, by reacting the ketones which, falling within general formula (II), correspond to the general formula

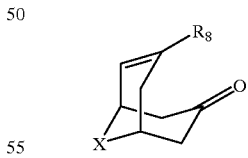

enriched in one or other of the enantiomers, with the aminonitriles of general formula (III), in the manner already explained for obtaining the compounds of general formula (I) in racemic form.

The ketone (IIc) (which corresponds to the above formula with $X=CH_2$, $R_8=CH_2CH_3$), as well as other ketones related to this compound, may be obtained in a form enriched in one or other of the enantiomers via the reaction sequence in the following scheme:

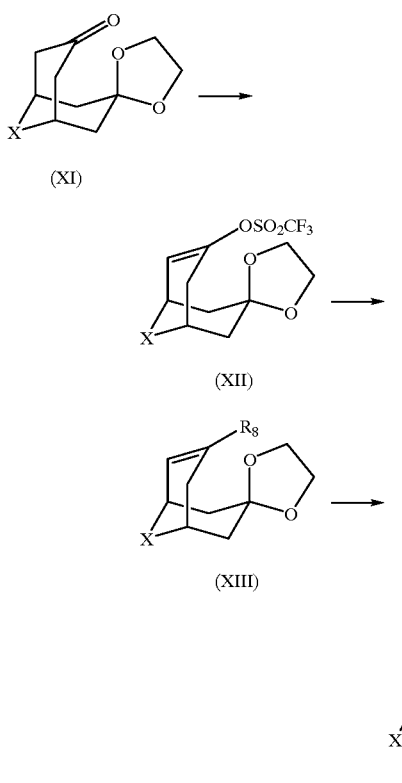

Achiral compound (XI)     (XII), (XIII) and (II) Chiral compounds enriched in one of the enantiomers The compounds (XI), in which X can adopt one of the meanings indicated above (for example X=CH$_2$, orthophenylene, and the like), may be obtained by acetalization of the corresponding compounds (VI) with ethylene glycol or other appropriate reagents, according to processes described [T. Momose and O. Muroaka, Chem. Pharm. Bull. 26, 288–295 (1978)], and are the achiral starting materials of this enantioselective synthetic sequence. Reaction of the achiral ketone acetals (XI) with a lithium amide derived from a chiral amine in enantiomerically pure form, for example (+)—bis[(R)—1—phenylethyl]amine, in accordance with the procedure described for related cases [N. S. Simpkins et al., Tetrahedron 49, 207–218 (1993) and references cited therein] leads to enolate anions which are highly enriched in one of the enantiomers, by enantioselective abstraction of a proton from one or other of the α-carbonyl positions, which, on reaction with N-phenyl-bis (trifluoromethylsulphonyl)imide [J. E. McMurry and W. J. Scott, Tetrahedron Lett. 24, 979–982 (1983)] or with trifluoromethanesulphonic anhydride [P. J. Stang and W. Treptow, Synthesis, 283–284 (1980)], give the corresponding enol trifluoromethane-sulphonates (XII) enriched in one or other enantiomer, depending on the configuration of the starting amine. These enol trifluoromethane-sulphonates (XII), on reaction with Grignard reagents in the presence of Cu(I) complexes, lead to the acetals (XIII) in which R$_8$ represents an alkyl or aralkyl group, with the meaning given above in the context of R, or a phenyl or substituted phenyl group as defined above in the context of R4. The enantiomeric excess of the acetals (XIII) is substantially the same as that of their precursors (XII), that is to say this reaction proceeds with little or no epimerization [for a related reaction, see: J. Kant, J. Org. Chem. 58, 2296–2301 (1993)].

Hydrolysis of these acetals leads to the corresponding ketones (II), which process, under the reaction conditions described in Examples 33 and 34, also proceeds with little or no epimerization, so that the enantiomeric excess of the ketones (II) is similar to that of the precursor acetals (XIII).

Reaction of these ketones (II) enriched in one or other of the enantiomers with the aminonitriles (III), under the conditions described above starting from the racemic ketones (II), leads to the aminoquinolines (I) enriched in one or other enantiomer depending on the ketone (II) used, although the enantiomeric excess of the aminoquinoline (I) obtained is normally less than that of the starting ketone (II) owing to the epimerization of the latter prior to the condensation. By fractional crystallization of these aminoquinolines or their salts, for example the corresponding hydrochlorides, the aminoquinolines (I) may be obtained enantiomerically pure or highly enriched in one or other of the enantiomers.

The compounds of general formula (I) which are the subject of the present invention display marked inhibitory activity against the enzyme acetylcholinesterase, some of them being considerably more active than tacrine, a known inhibitor of the abovementioned enzyme which is already used as a therapeutic agent in cases of senile dementia or Alzheimer's disease.

The compounds which are the subject of the invention, as well as their addition salts with pharmaceutically acceptable acids, may be administered orally or parenterally in the form of conventional pharmaceutical preparations such as tablets, capsules, syrups and suspensions. Alternatively, they may be administered parenterally in the form of solutions or emulsions, and the like. They may be applied directly to the rectum in the form of suppositories. The preparations can contain carriers which are physiologically acceptable, excipients, activators, chelating agents, stabilizers, and the like. In the case of injections, buffers which are physiologically acceptable, solubilizing agents or tonicity agents may be incorporated. The daily dose can vary depending on the symptoms of the disease, the patients' age and body weight, the mode of administration, and the like, and the normal dose for an adult person can be between 1 and 500 mg daily divided into several portions.

A series of examples, which should be interpreted as illustrative of the subject of the present invention and not as limiting the scope thereof, are described below.

EXAMPLES

The melting points of the compounds were determined on a Gallenkamp model MFB.595.010M apparatus. IR spectra were recorded on a Perkin Elmer FT-IR model 1600 spectrophotometer. Thin-layer chromatography was performed on silica gel 60 F254 (Alugran R sil G/UV254). For column chromatography, silica gel 60 (Merck, 230–440 mesh) was used. Microanalyses were performed in the Microanalysis Department of the Centro de Investigación y Desarrollo [Research and Development Centre], C.I.D., Barcelona, Spain, and agree with the theoretical values with an error of ±0.3% except where otherwise stated. In general, the compounds were dried in vacuo (1 Torr) at 80° C. for 2 days (standard conditions).

NMR ($^{13}$C and $^1$H) spectra were recorded on Varian Gemini 200 and 300 and Varian VXR 500 spectrometers; chemical shifts are given in ppm with respect to TMS (δ scale); coupling constants are expressed in hertz (Hz) and standard abbreviations have been used. $^1$H/$^1$H COSY experiments were performed using standard procedures, and $^1$H/$^{13}$C experiments using HMQC and HMBC pulse sequences with an indirect detection probe. Tables 4(1), 4(2), 5(1), 5(2), 6, 7(1) and 7(2) show the chemical shifts and coupling constants of the compounds of general formula (I) obtained in Examples 1 to 24. The ring carbons are identified with a lower-case letter in accordance with the following ring structures, to which all the compounds obtained in the abovementioned examples can be assigned. The enantiomeric excesses of the compounds (+)— and (−)—Ibw, (+)— and (−)—Icw and (+)— and (−)—XII (X=CH$_2$) were established by high performance liquid-liquid chromatography (HPLC) using a Waters 600 instrument and the CHIRALCEL OD—H column (25×0.46 cm) from Daicel Co. Ltd., containing the chiral stationary phase cellulose tris(3,5-dimethylphenylcarbamate). The enantiomeric excesses of the compounds (+)— and (−)—XIII (X=CH$_2$, R$_8$=CH$_2$CH$_3$) and (+)— and (−)—II (X=CH$_2$, R$_8$=CH$_2$CH$_3$) were established by gas-liquid chromatography (CG) using a Perkin-Elmer mod. 8600 instrument with an SU PELCO β-DEX 110-column (30 m×0.25 mm) containing β-cyclodextrin as chiral stationary phase. The compounds (±)—Ibw and (±)—Icw were separated by medium pressure liquid-liquid chromatography (MPLC) using a Buchi instrument with a column (23×2.6 cm) containing microcrystalline cellulose triacetate (15–25 µm) from the company Merck as chiral stationary phase, eluting with 96% ethanol.

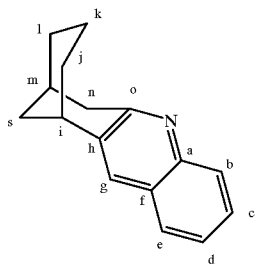

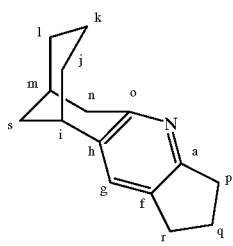

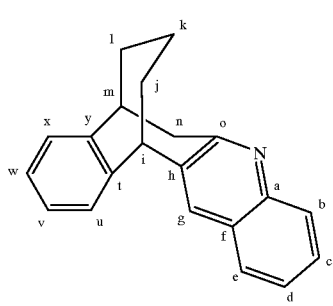

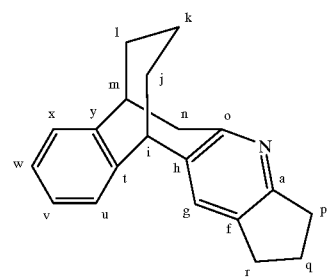

TABLE 4(1)

Chemical shifts in $^{13}$C NMR (δ, ppm)[a,b] of the hydrochlorides of the compounds:

| | Iaw | Ibw | Ibx[c] | Iby[d] | Icy[e] | Icw | Icx[e,f] |
|---|---|---|---|---|---|---|---|
| C-a | 139.0 | 138.6 | 140.5 | 140.4 | 139.7 | 138.8 | 140.6 |
| C-b | 120.1 | 119.8 | 116.2 | 104.8 | 119.4 | 120.0 | 116.3 |
| C-c | 134.4 | 134.1 | 134.9 | 166.2 | 140.4 | 134.4 | 135.0 |
| C-d | 127.1 | 127.0 | 112.2 | 116.5 | 127.6 | 127.1 | 112.2 |
| C-e | 114.2 | 124.2 | 161.1 | 127.8 | 126.3 | 124.2 | 161.2 |
| C-f | 116.8 | 116.5 | 107.3 | 113.7 | 115.5* | 116.7 | 107.3 |
| C-g | 157.3 | 156.3 | 152.9 | 156.6* | 156.6# | 156.7 | 155.4* |
| C-h | 114.9 | 114.8 | 115.9 | 115.0 | 115.4* | 114.9 | 115.8 |
| C-i | 27.2 | 27.4 | 27.1 | 27.4 | 27.6 | 27.5 | 27.1 |
| C-j | 31.2 | 35.9 | 35.6 | 35.9 | 34.2 | 34.3 | 34.0 |
| C-k | 127.4 | 134.8 | 134.9 | 134.8 | 140.4 | 140.4 | 140.4 |
| C-l | 131.0 | 125.0 | 125.0 | 125.0 | 123.3 | 123.3 | 123.2 |
| C-m | 28.0 | 28.0 | 28.0 | 28.1 | 28.1 | 28.1 | 27.9 |
| C-n | 35.6 | 35.8 | 35.8 | 35.9 | 36.1 | 36.0 | 35.9 |
| C-o | 152.3 | 152.1 | 155.3 | 153.0* | 153.2# | 152.3 | 152.9* |
| C-s | 29.2 | 29.2 | 29.2 | 29.2 | 29.4 | 29.5 | 29.4 |
| k-CH$_3$ | | 23.5 | 23.5 | 23.5 | 12.6 | 12.6 | 12.5 |
| k-CH$_2$—Me | | | | | 30.9 | 30.9 | 30.9 |

[a]The values marked with * or # within one and the same column are interchangeable.
[b]Except where otherwise stated, the spectra were recorded at 50.3 MHz in CD$_3$OD.
[c]For this compound, the following coupling constants were observed in addition: J$_{c-a/F}$ = 4.5; J$_{C-b/F}$ = 3.9; J$_{C-c/F}$ = 11.2: J$_{C-d/F}$ = 23.8; J$_{C-e/F}$ = 252.8; J$_{C-f/F}$ = 11.5.
[d]For this compound, the following coupling constants were observed in addition: J$_{C-a/F}$ = 12.6; J$_{C-b/F}$ = 25.5; J$_{C-c/F}$ = 254.1; J$_{C-d/F}$ = 24.6; J$_{C-e/F}$ = 10.5.
[e]This spectrum was recorded at 75.4 MHz;
[f]For this compound, the following coupling constants were observed in addition; J$_{C-c/F}$ = 11.5; J$_{C-d/F}$ = 23.0; J$_{C-e/F}$ = 252.5; J$_{C-f/F}$ = 19.0.

TABLE 4(2)

Chemical shifts in $^{13}$C NMR (δ, ppm)[a,b] of the hydrochlorides of the compounds:

| | Icy[c,d] | Idw[c] | Iew | Ifw[e] | Iiw | Ijw | Ikw[f] |
|---|---|---|---|---|---|---|---|
| C-a | 140.4 | 138.8 | 138.9 | 138.6 | 139.3 | 139.0 | 143.6 |
| C-b | 104.8 | 120.0 | 120.0 | 119.7 | 120.6 | 120.1 | 125.3 |
| C-c | 166.3 | 134.3 | 134.4 | 134.0 | 134.0 | 134.6 | 139.8 |
| C-d | 116.6 | 127.1 | 127.1 | 126.8 | 126.9 | 127.3 | 132.6 |
| C-e | 127.8 | 124.2 | 124.2 | 124.0 | 124.0 | 124.2 | 128.9 |
| C-f | 113.7 | 116.7 | 116.7 | 116.5 | 116.9 | 116.6 | 121.5 |
| C-g | 156.7* | 156.6* | 156.7* | 156.5 | 156.5 | 157.4 | 162.0 |
| C-h | 115.0 | 114.9 | 114.9 | 114.3 | 113.7 | 114.8 | 119.0 |
| C-i | 27.4 | 27.6 | 27.6 | 27.2 | 35.6 | 36.9 | 44.1 |
| C-j | 34.3 | 34.0 | 34.0 | 33.0 | 35.8 | 33.8 | 40.9 |
| C-k | 140.3 | 138.6 | 138.8 | 137.2 | 134.0 | — | 140.6 |
| C-l | 123.3 | 124.9 | 124.8 | 127.0 | 125.2 | 122.9 | 129.2 |
| C-m | 28.0 | 28.2 | 28.2 | 28.3 | 37.8 | 36.1 | 44.7 |
| C-n | 36.0 | 36.0 | 36.1 | 35.4 | 33.3 | 35.2 | 40.6 |

TABLE 4(2)-continued

Chemical shifts in $^{13}$C NMR ($\delta$, ppm)[a,b] of the hydrochlorides of the compounds:

| | Icy[c,d] | Idw[c] | Iew | Ifw[e] | Iiw | Ijw | Ikw[f] |
|---|---|---|---|---|---|---|---|
| C-o | 153.0* | 152.3* | 152.4* | 151.5 | 153.1 | 151.1 | 156.6 |
| C-s | 29.4 | 29.5 | 29.5 | 28.9 | 74.5 | 74.1 | 100.4 |
| k-CH$_3$ | 12.5 | 13.7 | 14.1 | | 22.7 | 23.1 | 28.6 |
| k-CH$_2$—Me | 30.9 | 21.6 | 23.0 | | | | |
| k-CH$_2$—Et | | 40.3 | 30.8 | | | | |
| k-CH$_2$—Pr | | | 37.9 | | | | |
| k-Cipso | | | | 141.7 | | | |
| k-ortho | | | | 125.8 | | | |
| k-Cmeta | | | | 129.1 | | | |
| k-cpara | | | | 128.1 | | | |
| s-CH$_3$ | | | | | | 19.8 | 20.2 |
| s-OCH$_3$ | | | | | | 49.3 | 49.7 |

[a]The values marked with * within one and the same column are interchangeable.
[b]Except where otherwise stated, the spectra were recorded at 50.3 MHz in CD$_3$OD.
[c]This spectrum was recorded at 75.4 MHz.
[d]For this compound the following coupling constants were observed in addition: $J_{C-b/F}$ = 25.2; $J_{C-c/F}$ = 253.9; $J_{C-d/F}$ = 24.7; $J_{C-e/F}$ = 10.7.
[e]This spectrum was recorded in a mixture of CD$_3$OD and CDCl$_3$.
[f]This spectrum was recorded at 75.4 MHz in D$_2$O.

TABLE 5(1)

$^1$H NMR data [chemical shifts ($\delta$, ppm)[a] and coupling constants (J, Hz)] of the hydrochlorides of the compounds:

| | Iaw | Ibw | Ibx | Iby | Icy | Icw | Icx |
|---|---|---|---|---|---|---|---|
| Chemical shifts $\delta$, ppm | | | | | | | |
| b-H | 7.72 | 7.73 | 7.56 | 7.42 | 7.75 | 7.72 | 7.57 |
| c-H | 7.79 | 7.85 | 7.82 | | | 7.86 | 7.82 |
| d-H | 7.55 | 7.60 | 7.33 | 7.42 | 7.56 | 7.61 | 7.33 |
| e-H | 8.31 | 8.34 | | 8.43 | 8.34 | 8.34 | |
| i-H | 3.35 | 3.39 | 3.38 | 3.37 | 3.38 | 3.40 | 3.40 |
| j-Hexo | 2.51 | 2.51 | 2.51 | 2.51 | 2.53 | 2.53 | 2.54 |
| j-Hendo | 2.08 | 1.98 | 1.98 | 1.97 | 2.00 | 2.02 | 2.02 |
| k-H | 5.64 | | | | | | |
| l-H | 5.82 | 5.57 | 5.57 | 5.57 | 5.56 | 5.58 | 5.58 |
| m-H | 2.77 | 2.78 | 2.77 | 2.78 | 2.80 | 2.80 | 2.80 |
| n-Hexo | 3.20 | 3.20 | 3.19 | 3.19 | 3.20 | 3.21 | 3.21 |
| n-Hendo | 2.92 | 2.88 | 2.86 | 2.85 | 2.87 | 2.87 | 2.88 |
| NH$_2$ | 4.95 | 4.82 | 4.87 | 4.87 | 4.82 | 4.87 | 4.83 |
| NH$^+$ | 4.95 | 4.82 | 4.87 | 4.87 | 4.82 | 4.87 | 4.83 |
| k-CH$_3$ | | 1.57 | 1.59 | 1.57 | 0.89 | 0.89 | 0.91 |
| k-CH$_2$—Me | | | | | 1.86 | 1.88 | 1.89 |
| s-Hsyn | 1.96 | 1.95 | 1.95 | 1.94 | 1.95 | 1.97 | 1.97 |
| s-Hanti | 2.11 | 2.07 | 2.08 | 2.07 | 2.07 | 2.08 | 2.09 |
| Coupling constants (J, Hz) | | | | | | | |
| b-H/C-H | 8.0 | 8.5 | 8.5 | | | 8.5 | 8.5 |
| b-H/d-H | 1.0 | 1.0 | 1.0 | | 1.5 | 1.0 | 0.5 |
| c-H/d-H | 7.0 | 7.0 | 8.5 | | | 7.0 | 8.5 |
| c-H/e-H | 1.0 | 1.5 | | | 1.5 | | |
| c-H/e-F | | | 5.5 | | | | 5.5 |
| d-H/e-H | 8.5 | 8.5 | | 10.0 | 9.0 | 8.5 | |
| d-H/e-F | | | 14.0 | | | | 14.0 |
| e-H/c-F | | | | | 5.5 | | |
| i-H/J-Hexo | | 4.5 | 4.5 | 4.5 | 4.5 | 5.5 | 5.0 |
| j-Hexo/j-Hendo | 18.0 | 18.0 | 18.0 | 18.0 | 17.5 | 18.0 | 17.5 |
| j-Hexo/k-H | 5.0 | | | | | | |
| k-H/l-H | 9.5 | | | | | | |
| l-H/m-H | | 4.5 | 5.0 | 4.5 | 5.5 | 5.5 | 5.5 |
| m-H/n-Hexo | 5.5 | 5.5 | 5.5 | 5.5 | 5.5 | 5.5 | 5.5 |
| m-H/n-Hendo | 1.5 | 2.0 | 2.0 | 2.0 | | 2.0 | |
| n-Hexo/n-Hendo | 18.0 | 18.0 | 18.0 | 18.0 | 18.0 | 18.0 | 18.0 |

TABLE 5(1)-continued $^1$H NMR data [chemical shifts ($\delta$, ppm)[a] and coupling constants (J, Hz)] of the hydrochlorides of the compounds:

| | Iaw | Ibw | Ibx | Iby | Icy | Icw | Icx |
|---|---|---|---|---|---|---|---|
| n-Hendo/S-Hanti | 1.5 | 2.0 | 2.0 | 2.0 | | 2.0 | |
| s-Hsyn/s-Hanti | 13.0 | 12.5 | 13.0 | 12.5 | 12.5 | 13.0 | 12.5 |

[a]Except where otherwise stated, the spectra were recorded at 500 MHz in CD$_3$OD.

TABLE 5(2)

$^1$H NMR data [chemical shifts ($\delta$, ppm)[a] and coupling constants (J, Hz)] of the hydrochlorides of the compounds:

| | Icy | Idw | Iew | Ifw[b] | Iiw | Ijw | Ikw[c] |
|---|---|---|---|---|---|---|---|
| Chemical shifts $\delta$ ppm | | | | | | | |
| b-H | 7.42 | 7.73 | 7.73 | 7.69 | 7.75 | 7.75 | 7.20 |
| c-H | | 7.86 | 7.85 | 7.28 | 7.85 | 7.87 | 7.43 |
| d-H | 7.42 | 7.61 | 7.61 | 7.11 | 7.60 | 7.62 | 7.20 |
| e-H | 8.44 | 8.34 | 8.35 | 8.02 | 8.34 | 8.36 | 7.70 |
| i-H | 3.39 | 3.40 | 3.41 | 3.26 | 3.33 | 3.28 | 3.08 |
| j-Hexo | 2.54 | 2.49 | 2.49 | 2.78 | 2.53 | 2.67 | 2.59 |
| j-Hendo | 2.01 | 2.02 | 2.03 | 2.42 | 2.07 | 1.82 | 2.01 |
| l-H | 5.58 | 5.57 | 5.56 | 6.11 | 5.53 | 5.41 | 5.43 |
| m-H | 2.81 | 2.80 | 2.80 | 2.86 | 2.67 | 2.67 | 2.65 |
| n-Hexo | 3.21 | 3.21 | 3.21 | 3.10 | 3.33 | 3.22 | 3.23 |
| n-Hendo | 2.86 | 2.88 | 2.87 | 3.03 | 2.80 | 3.00 | 2.84 |
| NH$_2$ | 4.84 | 4.87 | 4.87 | 2.43 | 4.82 | 4.82 | 4.64 |
| NH$^+$ | 4.84 | 4.87 | 4.87 | 2.43 | 4.82 | 4.82 | 4.64 |
| OH | | | | | | | 4.64 |
| k-CH$_3$ | 0.90 | 0.68 | 0.71 | | 1.57 | 1.56 | 1.50 |
| k-CH$_2$—Me | 1.88 | 1.29 | 1.07 | | | | |
| k-CH$_2$—Et | | 1.85 | 1.24 | | | | |
| k-CH$_2$—Pr | | | 1.88 | | | | |
| k-ortho-H | | | | 7.17 | | | |
| k-Cmeta-H | | | | 7.11 | | | |
| k-Cpara-H | | | | 7.06 | | | |
| s-Hsyn | 1.96 | 1.97 | 1.98 | 1.73 | | | |
| s-Hanti | 2.09 | 2.09 | 2.09 | 2.02 | | | |
| s-CH$_3$ | | | | | | 1.44 | 1.26 |
| s-OCH$_3$ | | | | | | 3.17 | 3.33 |
| Coupling constants (J, Hz) | | | | | | | |
| b-H/c-H | | 8.5 | 8.5 | 8.5 | 8.5 | 8.5 | 8.0 |
| b-H/d-H | | 1.0 | 1.0 | | 1.0 | 1.0 | |
| c-H/d-H | | 7.0 | 7.0 | | 7.0 | 7.0 | |
| c-H/e-H | | 1.5 | 1.0 | | 1.0 | 1.5 | |
| d-H/e-H | 10.0 | 8.5 | 8.5 | 8.5 | 8.5 | 8.5 | 8.5 |
| e-H/c-F | 5.5 | | | | | | |
| i-H/j-Hexo | 5.5 | 5.0 | 5.0 | 4.5 | 6.0 | | 5.5 |
| j-Hexo/j-Hendo | 18.0 | 18.0 | 17.5 | 17.5 | 18.5 | 17.0 | 18.0 |
| l-H/m-H | 5.5 | 5.5 | 5.5 | 6.0 | 6.0 | 6.0 | 5.5 |
| n-H/n-Hexo | 5.5 | 5.5 | 5.5 | 5.5 | | 6.0 | 6.0 |
| m-H/n-Hendo | 1.5 | 2.0 | 2.0 | | | 1.0 | 1.5 |
| n-Hexo/n-Hendo | 18.0 | 18.0 | 18.0 | 18.5 | 18.0 | 18.5 | 18.0 |
| n-Hendo/s-Hanti | 1.5 | 2.0 | 2.0 | | | | |
| s-Hsin/s-Hanti | 12.5 | 12.5 | 12.5 | 13.0 | | | |
| orto-H/meta-H | | | | 7.0 | | | |
| meta-H/para-H | | | | 7.5 | | | |

[a]Except where otherwise stated, the spectra were recorded at 500 MHz in CD$_3$OD.
[b]This spectrum was recorded in a mixture of CD$_3$OD and CDCl$_3$.
[c]This spectrum was recorded in D$_2$O.

TABLE 6

Chemical shifts in $^{13}$C NMR (δ, ppm)[a,b] of the hydrochlorides of the compounds:

| | Ibz | Igw | Ihw | Ilw[c] | Imw[c] | Inw | Iow | Iqw | Irw | Irz |
|---|---|---|---|---|---|---|---|---|---|---|
| C-a | 168.6# | 138.7 | 138.9 | 136.9* | 137.0* | 138.8 | 138.8 | 138.2 | 138.5 | 161.3* |
| C-b | | 120.0 | 120.1 | 120.0 | 120.0 | 119.9 | 119.9 | 119.6 | 120.0 | |
| C-c | | 134.3 | 134.5 | 134.4 | 134.2 | 134.6 | 134.6 | 134.0 | 133.6 | |
| C-d | | 126.9 | 127.2 | 127.2 | 127.2 | 127.4 | 127.3 | 127.0 | 126.6 | |
| C-e | | 124.2 | 124.2 | 124.2 | 124.2 | 124.4 | 124.3 | 124.2 | 124.0 | |
| C-f | 122.6* | 116.4 | 116.6 | 116.8 | 116.7 | 116.8 | 116.6 | 116.6 | 116.4 | 119.9 |
| C-g | 165.9# | 156.0 | 156.3 | 156.4# | 156.0# | 157.6 | 157.4* | 156.3* | 154.5* | 155.5* |
| C-h | 122.4* | 114.5 | 114.7 | 114.8 | 115.6 | 114.1 | 113.5 | 115.3 | 114.4 | 118.5 |
| C-i | 29.5 | 28.3 | 29.1 | 30.6 | 38.7 | 42.2 | 43.0 | 40.6 | 26.3 | 26.8 |
| C-j | 36.3 | 29.4 | 38.2 | 38.1 | 39.1 | 39.3 | 31.9 | 37.8 | 35.6# | 36.2 |
| C-k | 133.6 | 19.2 | 65.5 | 135.0* | 135.6* | 137.5 | 23.9 | 70.4 | 66.5 | 66.9 |
| C-l | 125.7 | 33.7 | 42.9 | 125.7 | 124.7 | 123.3 | 34.0 | 39.0 | 39.1 | 40.0 |
| C-m | 28.8 | 27.3 | 28.5 | 39.4 | 31.6 | 42.2 | 42.3 | 40.4 | 26.0 | 27.3 |
| C-n | 34.5 | 34.7 | 34.9 | 38.4 | 37.5 | 41.0 | 38.2 | 39.5 | 35.3# | 39.2 |
| C-o | 161.5# | 154.4 | 153.5 | 152.4# | 152.1# | 154.2 | 156.1* | 156.2* | 153.5* | 149.3* |
| k-CH$_3$ | 23.4 | | | 23.0 | 23.0 | 26.2 | | | | |
| C-p | 33.6 | | | | | | | | | 34.7 |
| C-q | 24.3 | | | | | | | | | 23.6 |
| C-r | 29.9 | | | | | | | | | 28.5 |
| C-s | 28.6 | 32.1 | 31.6 | 138.8* | 138.8* | | | | 31.9 | 32.4 |
| C-t | | | | | | 142.0 | 144.8 | 143.7 | | |
| C-u | | | | | | 128.1* | 130.0 | 129.9 | | |
| C-v | | | | | | 128.4* | 128.3 | 128.4 | | |
| C-w | | | | | | 129.0* | 128.9 | 129.1 | | |
| C-x | | | | | | 130.0* | 129.4 | 129.1 | | |
| C-y | | | | | | 145.2 | 145.0 | 144.6 | | |
| s-C$\underline{H}$CH$_3$ | | | | 116.5 | 116.6 | | | | | |
| s-CH—$\underline{C}$H$_3$ | | | | 12.5 | 12.5 | | | | | |

[a]The values marked with * or # within one and the same column are interchangeable.
[b]Except where otherwise stated, the spectra were recorded at 50.3 MHz in CD$_3$OD.
[c]This spectrum was recorded at 75.4 MHz.

TABLE 7(1)

Chemical shifts in $^1$H NMR (δ, ppm)[a,b] of the hydrochlorides of the compounds:

| | Ibz | Igw | Ihw | Ilw | Imw | Inw | Ipw | Iqw | Irw | Irz[c] |
|---|---|---|---|---|---|---|---|---|---|---|
| b-H | | 7.76 | 7.77 | 7.74 | 7.74 | 7.78 | 7.73 | 7.70 | 7.80 | |
| c-H | | 7.86 | 7.87 | 7.86 | 7.85 | 7.84 | 7.85 | 7.82 | 7.88 | |
| d-H | | 7.60 | 7.61 | 7.62 | 7.61 | 7.61 | 7.60 | 7.59 | 7.65 | |
| e-H | | 8.33 | 8.35 | 8.37 | 8.35 | 8.41 | 8.34 | 8.34 | 8.37 | |
| i-H | 3.13 | 3.28 | 3.38 | 4.33 | 3.74 | 4.62 | 4.59 | 4.54 | 3.32 | 2.96 |
| j-Hexo | 2.47 | 1.77 | 1.55 | 2.52 | 2.55 | 2.61 | 1.82 | 2.16 | 1.96–2.26 | 1.87 |
| j-Hendo | 1.89 | 1.72 | 2.35 | 2.20 | 2.19 | 2.50 | 2.17 | 2.33 | 1.96–2.26 | 1.99 |
| k-Hexo | | 1.53 | | | | | 1.82 | 4.25 | 4.21 | 4.04 |
| k-Hendo | | 1.18 | 3.46 | | | | 1.82 | | | |
| l-Hexo | 5.56 | 1.77 | 1.64 | 5.54 | 5.54 | 5.81 | 1.82 | 2.23 | 1.96–2.26 | 1.87 |
| l-Hendo | | 1.77 | 2.20 | | | | 2.17 | 2.30 | 1.96–2.26 | 1.99 |
| n-H | 2.73 | 2.44 | 2.62 | 3.13 | 3.64 | 3.74 | 3.39 | 3.49 | 3.61 | 2.36 |
| n-Hexo | 2.95 | 2.35 | 3.34 | 3.17 | 3.15 | 3.38* | 3.51 | 3.44 | 3.40 | 3.02 |
| n-Hendo | 2.58 | 2.86 | 2.92 | 3.05 | 3.08 | 3.54* | 3.47 | 3.66 | 3.18 | 2.85 |
| NH$_2$ | 4.82 | 4.82 | 4.81 | 4.83 | 4.83 | 4.85 | 4.82 | | 4.98 | 4.89 |
| NH$^+$ | 4.82 | 4.82 | 4.81 | 4.83 | 4.83 | 4.85 | 4.82 | | 4.98 | 4.89 |
| OH | | | 4.81 | | | | | | 4.98 | 4.89 |
| k-CH$_3$ | 1.60 | | | 1.56 | 1.56 | 1.62 | | | | |
| p-H$_2$ | 3.06 | | | | | | | | | 2.80 |
| q-H$_2$ | 2.27 | | | | | | | | | 2.07 |
| r-H$_2$ | 2.85 | | | | | | | | | 2.70 |
| s-Hsyn | 1.83 | 1.89 | 1.88* | | | | | | 1.96–2.26 | 1.79 |
| s-Hanti | 1.91 | 2.04 | 1.99* | | | | | | 1.96–2.26 | 1.87 |
| u-H | | | | | | 7.21# | 7.27 | 7.27 | | |
| v-H | | | | | | 7.21# | 7.15 | 7.17 | | |
| w-H | | | | | | 7.21# | 7.20 | 7.23 | | |
| x-H | | | | | | 7.33# | 7.24 | 7.26 | | |

TABLE 7(1)-continued

Chemical shifts in $^1$H NMR ($\delta$, ppm)[a,b] of
the hydrochlorides of the compounds:

| | Ibz | Igw | Ihw | Ilw | Imw | Inw | Ipw | Iqw | Irw | Irz[c] |
|---|---|---|---|---|---|---|---|---|---|---|
| s-C$\underline{H}$CH$_3$ | | | | 5.52 | 5.54 | | | | | |
| s-CHC$\underline{H}_3$ | | | | 1.76 | 1.71 | | | | | |

[a]The values marked with * or # within one and the same column are interchangeable.
[b]Except where otherwise stated, the spectra were recorded at 500 MHz in CD$_3$OD.
[c]This spectrum was recorded at 300 MHz.

TABLE 7(2)

Coupling constants in $^1$H NMR (J, Hz)[a,b]
of the hydrochlorides of the compounds:

| | Ibz | Igw[c] | Ihw[d] | Ilw | Imw | Inw | Ipw | Iqw[e] | Irw[f] | Irz[f] |
|---|---|---|---|---|---|---|---|---|---|---|
| b-H/c-H | | 8.5 | 9.0 | 8.0 | 8.5 | 8.0 | 9.5 | 9.5 | 9.4 | |
| b-H/d-H | | 1.0 | 1.0 | 1.0 | 1.5 | 1.0 | 1.0 | 1.0 | 1.5 | |
| c-H/d-H | | 7.0 | 7.0 | 7.0 | 7.0 | 7.0 | 7.0 | 7.0 | 7.0 | |
| c-H/e-H | | 2.0 | 1.0 | 1.0 | 1.5 | 1.0 | 1.5 | 1.0 | 1.5 | |
| d-H/e-H | | 8.5 | 8.5 | 8.0 | 8.5 | 8.5 | 8.5 | 8.5 | 8.4 | |
| i-H/j-Hexo | 4.5 | | 4.0 | 5.5 | 5.5 | 4.0 | 1.5 | 4.0 | | |
| i-H/j-Hendo | | | | | | 4.0 | 6.5 | 5.0 | | |
| j-Hexo/j-Hendo | 17.5* | 13.5 | 12.0 | 17.5 | 17.0 | 18.5 | | 14.5 | | |
| l-Hexo/l-Hendo | | | 12.0 | | | | | 15.0 | | |
| l-Hexo-m-H | 4.5 | | 4.0 | 5.5 | | 8.5 | | 3.5 | | |
| l-Hendo-m-h | | | | | | | | 5.0 | | |
| n-H/n-Hexo | 5.5 | 7.5 | 8.5 | 5.5 | 5.0 | 4.0* | 5.5 | 5.5 | 7.5 | 7.5 |
| n-H/n-Hendo | | | | | 2.0 | 4.5* | 3.0 | 2.5 | | |
| n-Hexo/n-Hendo | 18.5 | 19.0 | 19.0 | 17.0 | 17.5 | 18.0 | 19.0 | 18.0 | 18.6 | 17.5 |
| n-Hsyn/s-Hanti | 12.5 | 13.0 | 13.0 | | | | | | | 13.0 |
| u-H/v-H | | | | | | | | 7.5 | 7.5 | |
| u-H/w-H | | | | | | | | 1.5 | 1.5 | |
| v-H/w-H | | | | | | | | 7.5 | 7.5 | |
| v-H/x-H | | | | | | | | 1.5 | 1.5 | |
| w-H/x-H | | | | | | | | 7.5 | 7.5 | |

[a]The values marked with * within one and the same column are interchangeable.
[b]Except where otherwise stated, the spectra were recorded at 500 MHz in CD$_3$OD.
[c]For this compound, the following coupling constants were observed in addition: j-Hendo/k-Hexo = j-Hendo/k-Hendo = 4.0; k-Hexo/k-Hendo = 14.5.
[d]For this compound, the following coupling constants were observed in addition: j-Hexo/k-Hendo = 12.0; k-Hendo/l-Hexo = 12.0.
[e]For this compound, the following coupling constants were observed in addition: j-Hexo/k-H = 4.0; j-Hendo/k-H = k-H/l-Hendo = 5.0; j-Hendo/l-Hendo = 1.5; k-H/l-Hexo = 3.5.
[f]This spectrum was recorded at 300 MHz.

Example 1

12-Amino-6,7,10,11-tetrahydro-7,11-methanocycloocta[b]-quinoline, Iaw.

A suspension was prepared of AlCl$_3$ (489 mg, 3.67 mmol) and 2-aminobenzonitrile (437 mg, 3.70 mmol) in 1,2-dichloroethane (120 ml) under argon, and was cooled in an ice bath. A solution of ketone IIa (500 mg, 3.67 mmol) in 1,2-dichloroethane (20 ml) was added dropwise and the reaction mixture was heated to reflux for 1 h. The resulting suspension was cooled to 0° C., treated dropwise with a mixture of THF (120 ml) and water (60 ml) and alkalinized with 2 N aqueous NaOH solution, the mixture being left stirring for 30 minutes. On evaporation of the organic solvent at reduced pressure and filtration of the resulting mixture, a yellowish solid (1.20 g) separated and was subjected to column chromatography on silica gel (25 g) using hexane/ethyl acetate/methanol mixtures of increasing polarity as eluent. On elution with 90:10 ethyl acetate/methanol, Iaw (510 mg, 59% yield) was obtained.

Iaw.HCl: Concentrated HCl (10 ml) was added to a solution of Iaw (510 mg) in methanol (50 ml) and the mixture was heated to reflux for 20 minutes. On evaporation of the solvent to dryness, a yellowish solid (520 mg) was obtained, which was crystallized from 1:1 ethyl acetate/methanol (15 ml) to give, after drying at 80° C./1 Torr for 2 days (standard conditions), Iaw.HCl.1.75H$_2$O, (310 mg, 28% overall yield) in the form of a white solid, m.p. 177–179° C. (ethyl acetate/methanol) (dec.); IR (KBr) v: 3700–2000 (maxima at 3335 and 3176, NH, OH and NH$^+$ st), 1652 and 1586 (ar—C—C and ar—C—N st) cm$^{-1}$. The elemental analysis was in agreement with C$_{16}$H$_{16}$N$_2$.HCl.1.75H$_2$O.

Example 2

12-Amino-6,7,10,11-tetrahydro-9-methyl-7,11-methanocycloocta[b]quinoline, Ibw.

This reaction was performed in a manner similar to that described for the preparation of Iaw, starting from AlCl$_3$ (1.5 g, 11.2 mmol), 2-aminobenzonitrile (1.15 g, 9.73 mmol), 1,2-dichleroethane (120 ml) and a solution of ketone IIb (1.5 g, 9.79 mmol) in 1,2-dichloroethane (20 ml). The yellowish solid residue obtained (2.5 g) was subjected to column chromatography on silica gel (50 g) using hexane/ethyl acetate/methanol mixtures of increasing polarity as eluent. On elution with 90:10 ethyl acetate/methanol, Ibw (1.48 g, 60% yield) was obtained.

Ibw.HCl: This was prepared from Ibw (1.48 g) in a manner similar to that described for Iaw.HCl. After evaporation of the acid solution to dryness, the dark solid obtained (1.50 g) was decolorized with active charcoal, and the resulting light brown residue (1.20 g) was crystallized from 1:1 ethyl acetate/methanol (20 ml) to give, after drying under the standard conditions, Ibw.HCl.H$_2$O(980 mg, 33% overall yield) in the form of a white solid, m.p. 265–268° C. (ethyl acetate/methanol) (dec.); IR (KBr) v: 3700–2000 (maxima at 3354 and 3202, NH, OH and NH$^+$ st), 1640 and 1588 (ar—C—C and ar—C—N st) cm$^{-1}$. The elemental analysis was in agreement with $C_{17}H_{18}N_2.HCl.H_2O$.

Example 3

12-Amino-1-fluoro-6,7,10,11-tetrahydro-9-methyl-7,11-methanocycloocta[b]quinoline, Ibx.

This reaction was performed in a manner similar to that described for the preparation of Iaw, starting from AlCl$_3$ (900 mg, 6.75 mmol), 2-amino-6-fluorobenzonitrile (1.00 g, 7.35 mmol), 1,2-dichloroethane (120 ml) and a solution of ketone IIb (1.00 g, 6.67 mmol) in 1,2-dichloroethane (20 ml). The yellowish solid residue obtained (1.80 g) was subjected to column chromatography on silica gel (50 g) using hexane/ethyl acetate/methanol mixtures of increasing polarity as eluent. On elution with 90:10 ethyl acetate/methanol, Ibx (1.18 g, 66% yield) was obtained.

Ibx.HCl: This was prepared from Ibx (1.18 g) in a manner similar to that described for Iaw.HCl. After evaporation of the acid solution to dryness, the dark solid obtained (1.20 g) was decolorized with active charcoal, and the residue obtained (1.00 g) was crystallized from 1:1 ethyl acetate/methanol (30 ml) to give, after drying under the standard conditions, Ibx.HCl (459 mg, 23% overall yield) in the form of a pinkish white solid, m.p. 268° C. (ethyl acetate/methanol) (dec.); IR (KBr) v: 3700–2000 (maxima at 3408 and 3161, NH and NH$^+$ st), 1639 and 1595 (ar—C—C and ar—C—N st) cm$^{-1}$. The elemental analysis was in agreement with $C_{17}H_{17}FN_2.HCl$.

Example 4

12-Amino-3-fluoro-6,7,10,11-tetrahydro-9-methyl-7,11-methanocycloocta[b]quinoline, Iby.

This reaction was performed in a manner similar to that described for the preparation of Iaw, starting from AlCl$_3$ (2.8 g, 21.0 mmol), 2-amino-4-fluorobenzonitrile (2.0 g, 14.5 mmol), 1,2-dichloroethane (20 ml) and a solution of ketone IIb (1.71 g, 11.4 mmol) in 1,2-dichloroethane (120 ml), and heating the reaction mixture to reflux for 7 h. The solid residue obtained (4.45 g) was subjected to column chromatography on silica gel (110 g) using hexane/ethyl acetate/methanol mixtures of increasing polarity as eluent. On elution with 70:30 ethyl acetate/methanol, Iby (2.27 g, 74% yield) was obtained.

Iby.HCl: A solution of Iby (2.09 g) in methanol (20 ml) was acidified with a solution of HCl in diethyl ether. After evaporation of the acid solution to dryness, the solid obtained (2.54 g) was crystallized from 1:3 methanol/water (20 ml) to give, after drying under the standard conditions, Iby.HCl.2/3H$_2$O, (1.40 g, 42% overall yield) in the form of a white solid, m.p. 220–222° C. (methanol/water; IR (KBr) v: 3700–2000 (maxima at 3334, 3176 and 2926, NH, OH and NH$^+$ st), 1638 and 1591 (ar—C—C and ar—C—N st) cm$^{-1}$. The elemental analysis was in agreement with $C_{17}H_{17}FN_2.HCl.2/3H_2O$.

Example 5

11-Amino-2,3,5,6,9,10-hexahydro-8-methyl-6,10-methano-1H-cycloocta[e]cyclopenta[b]pyridine, Ibz.

This reaction was performed in a manner similar to that described for the preparation of Iaw, starting from AlCl$_3$ (4.40 g, 33.0 mmol), 2-amino-1-cyclopentene-carbonitrile (3.57 g, 33.0 mmol), 1,2-dichloroethane (120 ml) and a solution of ketone IIb (4.90 g, 33.0 mmol) in 1,2-dichloroethane (80 ml), and heating the reaction mixture to reflux for 12 h. The yellowish solid residue obtained (6.50 g) was subjected to column chromatography on silica gel (100 g) using hexane/ethyl acetate/methanol mixtures of increasing polarity as eluent. On elution with 90:10 ethyl acetate/methanol, Ibz (760 mg, 10% yield) was obtained.

Ibz.HCl: This was prepared from Ibz (760 mg) in a manner similar to that described for Iaw.HCl. After evaporation of the acid solution to dryness, the solid obtained (863 mg) was crystallized from 1:1 ethyl acetate/methanol (30 ml) to give, after drying under the standard conditions, Ibz.HCl.3H$_2$O (410 mg, 4% overall yield) in the form of a white solid, m.p. 247–250° C. (ethyl acetate/methanol) (dec.); IR (KBr) v: 3700–2000 (maxima at 3341 and 3187, NH, OH and NH$^+$ st), 1655 and 1620 (ar—C—C and ar—C—N st) cm$^{-1}$. The elemental analysis was in agreement with $C_{16}H_{20}N_2.HCl.3H_2O$.

Example 6

12-Amino-3-chloro-9-ethyl-6,7,10,11-tetrahydro-7,11-methanocycloocta[b]quinoline, Icv.

This reaction was performed in a manner similar to that described for the preparation of Iaw, starting from AlCl$_3$ (3.00 g, 22.5 mmol), 2-amino-4-chlorobenzonitrile (2.33 g, 15.3 mmol), 1,2-dichloroethane (20 ml) and a solution of ketone IIc (1.80 g, 11.0 mmol) in 1,2-dichloroethane (115 ml), and heating the reaction mixture to reflux for 7 h. The solid residue obtained (4.2 g) was subjected to column chromatography on silica gel (125 g) using hexane/ethyl acetate mixtures of increasing polarity as eluent. On elution with 40:60 hexane/ethyl acetate, Icv (1.35 g, 41% yield) was obtained.

Icv.HCl: A solution of Icv (1.35 g) in methanol (30 ml) was acidified with a solution of HCl in methanol. After evaporation of the acid solution to dryness, the solid obtained (1.54 g) was crystallized from 3:10 methanol/water (26 ml) to give, after drying under the standard conditions, Icv.HCl.2/3H$_2$O, (0.96 g, 25% overall yield) in the form of a white solid, m.p. 202–206° C. (methanol/water) (dec.); IR (KBr) v: 3700–2000 (maxima at 3333, 3177, 2816 and 2671, NH, OH and NH$^+$ st), 1652, 1634 and 1585 (ar—C—C and ar—C—N st) cm$^{-1}$. The elemental analysis was in agreement with $C_{18}H_{19}ClN_2.HCl.2/3H_2O$.

Example 7

12-Amino-9-ethyl-6,7,10,11-tetrahydro-7,11-methanocycloocta[b]quinoline, Icw.

This reaction was performed in a manner similar to that described for the preparation of Iaw, starting from AlCl$_3$ (650 mg, 4.80 mmol), 2-aminobenzonitrile (567 mg, 4.87 mmol), 1,2-dichloroethane (120 ml) and a solution of ketone IIc (800 mg, 4.87 mmol) in 1,2-dichloroethane (20 ml). The yellowish solid residue obtained (1.50 g) was subjected to column chromatography on silica gel (25 g) using hexane/ethyl acetate/methanol mixtures of increasing polarity as eluent. On elution with 90:10 ethyl acetate/methanol, Icw (750 mg, 59% yield) was obtained.

Icw.HCl: This was prepared from Icw (750 mg) in a manner similar to that described for Iaw.HCl. After evaporation of the acid solution to dryness, the solid obtained (760 mg) was crystallized from 1:1 ethyl acetate/methanol (25 ml) to give, after drying under the standard conditions, Icw.HCl.1.25H$_2$O (330 mg, 21% overall yield) in the form of a white solid, m.p. 260–263° C. (ethyl acetate/methanol) (dec.); IR (KBr) v: 3700–2000 (maxima at 3325 and 3150, NH, OH and NH$^+$ st), 1660 and 1587 (ar—C—C and ar—C—N st) cm$^{-1}$. The elemental analysis was in agreement with C$_{18}$H$_{20}$N$_2$.HCl.1.25H$_2$O.

Example 8

12-Amino-9-ethyl-1-fluoro-6,7,10,11-tetrahydro-7,11-methanocycloocta[b]quinoline, Icx.

This reaction was performed in a manner similar to that described for the preparation of Iaw, starting from AlCl$_3$ (1.35 g, 10.1 mmol), 2-amino-6-fluorobenzonitrile (1.06 g, 7.79 mmol), 1,2-dichloroethane (10 ml) and a solution of ketone IIc (0.8.5 g, 5.18 mmol) in 1,2-dichloroethane (40 ml), and heating the reaction mixture to reflux for 21 h. The solid residue obtained (3.18 g) was subjected to column chromatography on silica gel (95 g) using hexane/ethyl acetate mixtures of increasing polarity as eluent. On elution with 30:70 hexane/ethyl acetate, Icx (0.43 g, 29% yield) was obtained.

Icx.HCl: A solution of Icx (0.43 g) in methanol (8 ml) was acidified with a solution of HCl in methanol. After evaporation of the acid solution to dryness, the solid obtained (0.47 g) was crystallized from acetonitrile (5 ml) to give, after drying under the standard conditions, Icx.HCl (0.24 g, 15% overall yield) in the form of a white solid, m.p. 164–166° C. (acetonitrile); IR (KBr) v: 3700–2000 (maxima at 3334, 3208, 2867 and 2823, NH and NH$^+$ st), 1638 and 1594 (ar—C—C and ar—C—N st) cm$^{-1}$.

Example 9

12-Amino-9-ethyl-3-fluoro-6,7,10,11-tetrahydro-7,11-methanocycloocta[b]quinoline, Icy.

This reaction was performed in a manner similar to that described for the preparation of Iaw, starting from AlCl$_3$ (1.30 g, 9.74 mmol), 2-amino-4-fluorobenzonitrile (0.93 g, 6.84 mmol), 1,2-dichloroethane (10 ml) and a solution of ketone IIc (0.80 g, 4.88 mmol) in 1,2-dichloroethane (55 ml), and heating the reaction mixture to reflux for 7 h. The solid residue obtained (1.57 g) was subjected to column chromatography on silica gel (50 g) using hexane/ethyl acetate mixtures of increasing polarity as eluent. On elution with 30:70 hexane/ethyl acetate, Icy (0.55 g, 40% yield) was obtained.

Icy.HCl: A solution of Icy (0.55 g) in methanol (10 ml) was acidified with a solution of HCl in methanol. After evaporation of the acid solution to dryness, the solid obtained (0.65 g) was crystallized from 1:6 methanol/water (10.5 ml) to give, after drying under the standard conditions, Icy.HCl.1/2H$_2$O (0.45 g, 28% overall yield) in the form of a white solid, m.p. 202–206° C. (methanol/water) (dec.); IR (KBr) v: 3700–2000 (maxima at 3332, 3180, 2823 and 2696, NH, OH and NH$^+$ st), 1640 and 1591 (ar—C—C and ar—C—N st) cm$^{-1}$. The elemental analysis was in agreement with C$_{18}$H$_{19}$FN$_2$.HCl.1/2H$_2$O.

Example 10

12-Amino-6,7,10,11-tetrahydro-9-propyl-7,11-methanocycloocta[b]quinoline, Idw.

This reaction was performed in a manner similar to that described for the preparation of Iaw, starting from AlCl$_3$ (2.75 g, 20.6 mmol), 2-aminobenzonitrile (1.85 g, 15.5 mmol), 1,2-dichloroethane (20 ml) and a solution of ketone IId (1.84 g, 10.3 mmol) in 1,2-dichloroethane (120 ml), and heating the reaction mixture to reflux for 7 h. The solid residue obtained (4.32 g) was subjected to column chromatography on silica gel (130 g) using hexane/ethyl acetate/ methanol mixtures of increasing polarity as eluent. On elution with 70:30 ethyl acetate/methanol, Idw (2.82 g, 98% yield) was obtained.

Idw.HCl: A solution of Idw (2.80 g) in methanol (15 ml) was acidified with a solution of HCl in diethyl ether. After evaporation of the acid solution to dryness, the solid obtained (1.87 g) was crystallized from 1:1 methanol/water (20 ml) to give, after drying under the standard conditions, Idw.HCl (1.20 g, 37% overall yield) in the form of a white solid, m.p. 331–333° C. (methanol/water) (dec.); IR (KBr) v: 3700–2000 (maxima at 3320, 3146 and 2820, NH and NH$^+$ st), 1662 and 1586 (ar—C—C and ar—C—N st) cm$^{-1}$. The elemental analysis was in agreement with C$_{19}$H$_{22}$N$_2$.HCl.

Example 11

12-Amino-9-butyl-6,7,10,11-tetrahydro-7,11-methanocycloocta[b]quinoline, Iew.

This reaction was performed in a manner similar to that described for the preparation of Iaw, starting from AlCl$_3$ (2.80 g, 21.0 mmol), 2-aminobenzonitrile (2.00 g, 16.95 mmol), 1,2-dichloroethane (20 ml) and a solution of ketone IIe (2.20 g, 11.4 mmol) in 1,2-dichloroethane (120 ml), and heating the reaction mixture to reflux for 7 h. The solid residue obtained (3.86 g) was subjected to column chromatography on silica gel (150 g) using hexane/ethyl acetate/ methanol mixtures of increasing polarity as eluent. On elution with 70:30 ethyl acetate/methanol, Iew (2.40 g, 72% yield) was obtained.

Iew.HCl: A solution of Iew (2.40 g) in methanol (15 ml) was acidified with a solution of HCl in diethyl ether. After evaporation of the acid solution to dryness, the solid obtained (2.66 g) was crystallized from 2:3 methanol/water (25 ml) to give, after drying under the standard conditions, Iew.HCl (1.08 g, 29% overall yield) in the form of a white solid, m.p. 328–330° C. (methanol/water) (dec.); IR (KBr) v: 3700–2000 (maxima at 3316, 3146, 2927, 2823 and 2691, NH and NH$^+$ st), 1663 and 1586 (ar—C—C and ar—C—N st) cm$^{-1}$. The elemental analysis was in agreement with C$_{20}$H$_{24}$N$_2$.HCl.

Example 12

12-Amino-9-phenyl-6,7,10,11-tetrahydro-7,11-methanocycloocta[b]quinoline, Ifw.

This reaction was performed in a manner similar to that described for the preparation of Iaw, starting from AlCl$_3$ (627 mg, 4.70 mmol), 2-aminobenzonitrile (554 mg, 4.69 mmol), 1,2-dichloroethane (120 ml) and a solution of ketone IIf (1.00 g, 4.71 mmol) in 1,2-dichloroethane (20 ml). The yellowish solid residue obtained (2.20 g) was subjected to column chromatography on silica gel (50 g) using hexane/ ethyl acetate/methanol mixtures of increasing polarity as eluent. On elution with 90:10 ethyl acetate/methanol, Ifw (730 mg, 50% yield) was obtained.

Ifw.HCl: This was prepared from Ifw (730 mg) in a manner similar to that described for Iaw.HCl. After evaporation of the acid solution to dryness, the pink solid obtained (750 mg) was crystallized from 1:1 ethyl acetate/methanol (10 ml) to give, after drying under the standard conditions, Ifw.HCl.1.25H$_2$O (610 mg, 35% overall yield) in the form of a white solid, m.p. 207° C. (ethyl acetate/methanol) (dec.); IR (KBr) v: 3700–2000 (maxima at 3330 and 3200, NH, OH and NH$^+$ st), 1647 and 1589 (ar—C—C and ar—C—N st) cm$^{-1}$. The elemental analysis was in agreement with C$_{22}$H$_{20}$N$_2$.HCl.1.25H$_2$O.

Example 13

12-Amino-6,7,8,9,10,11-hexahydro-7,11-methanocycloocta[b]quinoline, Igw.

This reaction was performed in a manner similar to that described for the preparation of Iaw, starting from $AlCl_3$ (964 mg, 7.23 mmol)., 2-aminobenzonitrile (856 mg, 7.25 mmol), 1,2-dichloroethane (120 ml) and a solution of ketone IIg (1.00 g, 7.24 mmol) in 1,2-dichloroethane (20 ml) and heating the reaction mixture to reflux for 12 h. The yellowish solid residue obtained (2.40 g) was subjected to column chromatography on silica gel (50 g) using hexane/ethyl acetate/methanol mixtures of increasing polarity as eluent. On elution with 90:10 ethyl acetate/methanol, Igw (430 mg, 25% yield) was obtained.

Igw.HCl: This was prepared from Igw (430 mg) in a manner similar to that described for Iaw.HCl. After evaporation of the acid solution to dryness, the solid obtained (445 mg) was crystallized from 1:1 ethyl acetate/methanol (10 ml) to give, after drying under the standard conditions, Igw.HCl.$H_2O$ (310 mg, 15% overall yield) in the form of a white solid, m.p. 254–256° C. (ethyl acetate/methanol) (dec.); IR (KBr) v: 3700–2000 (maxima at 3450, 3165 and 2815, NH, OH and $NH^+$ st), 1664, 1632 and 1585 (ar—C—C and ar—C—N st) $cm^{-1}$. The elemental analysis was in agreement with $C_{16}H_{18}N_2$.HCl.$H_2O$.

Example 14

12-Amino-6,7,8,9,10,11-hexahydro-7,11-methanocycloocta[b]quinolin-9-exo-ol, Ihw.

This reaction was performed in a manner similar to that described for the preparation of Iaw, starting from $AlCl_3$ (430 mg, 3.22 mmol), 2-aminobenzonitrile (382 mg, 3.23 mmol), 1,2-dichloroethane (120 ml) and a solution of ketone IIh (500 mg, 3.24 mmol) in 1,2-dichloroethane (20 ml). The yellowish solid residue obtained (1.10 g) was subjected to column chromatography on silica gel (50 g) using hexane/ethyl acetate/methanol mixtures of increasing polarity as eluent. On elution with methanol, Ihw (400 mg, 48% yield) was obtained.

Ihw.HCl: This was prepared from Ihw (400 mg) in a manner similar to that described for Iaw.HCl. After evaporation of the acid solution to dryness, the dark solid obtained (475 mg) was decolorized with active charcoal, and the resulting residue (380 mg) was crystallized from 1:9 ethyl acetate/methanol (10 ml) to give, after drying under the standard conditions, Ihw.HCl.1.5$H_2O$ (200 mg, 19% overall yield) in the form of a yellowish-white solid, m.p. 260° C. (ethyl acetate/methanol) (dec.); IR (KBr) v: 3700–2000 (maxima at 3342 and 3200, NH, OH and $NH^+$ st), 1654, 1640 and 1587 (ar—C—C and ar—C—N st) $cm^{-1}$. The elemental analysis was in agreement with $C_{16}H_{18}N_2O$.HCl.1.5$H_2O$.

Example 15 syn-12-Amino-6,7,10,11-tetrahydro-9,13-dimethyl-13-methoxy-7,11-methanocycloocta[b]quinoline, Iiw.

This reaction was performed in a manner similar to that described for the preparation of Iaw, starting from $AlCl_3$ (488 mg, 3.57 mmol), 2-aminobenzonitrile (422 mg, 3.57 mmol), 1,2-dichloroethane (40 ml) and a solution of ketone IIi (631 mg, 3.25 mmol) in 1,2-dichloroethane (80 ml), and heating the reaction mixture to reflux for 6 h. The brownish residue obtained (0.90 g) was subjected to column chromatography on silica gel using hexane/ethyl acetate/methanol mixtures of increasing polarity as eluent. On elution with 90:10 ethyl acetate/methanol, Iiw (470 mg, 49% yield) was obtained.

Iiw.HCl: A solution of Iiw (470 mg) in methanol (10 ml) was acidified with a solution of HCl in diethyl ether. After evaporation of the acid solution to dryness, the dark solid obtained (490 mg) was crystallized from 10:1 ethyl acetate/methanol (22 ml) to give, after drying under the standard conditions, Iiw.HCl (380 mg, 35% overall yield) in the form of a white solid, m.p. 265–270° C. (ethyl acetate/methanol) (dec.); IR (KBr) v: 3700–2000 (maxima at 3331 and 3144, NH and $NH^+$ st), 1659 and 1588 (ar—C—C and ar—C—N st) $cm^{-1}$. The elemental analysis was in agreement with $C_{19}H_{22}N_2O$.HCl.

Example 16 anti-12-Amino-6,7,10,11-tetrahydro-9,13-dimethyl-13-methoxy-7,11-methanocycloocta[b]quinoline, Ijw.

This reaction was performed in a manner similar to that described for the preparation of Iaw, starting from $AlCl_3$ (160 mg, 1.20 mmol), 2-aminobenzonitrile (140 mg, 1.19 mmol), 1,2-dichloroethane (10 ml) and a solution of ketone IIj (200 mg, 1.03 mmol) in 1,2-dichloroethane (30 ml), and heating the reaction mixture to reflux for 4 h. The yellowish solid residue obtained (204 mg) was subjected to column chromatography on silica gel using hexane/ethyl acetate/methanol mixtures of increasing polarity as eluent. On elution with 95:5 ethyl acetate/methanol, Ijw (87 mg, 29% yield) was obtained.

Ijw.HCl: A solution of Ijw (87 mg) in methanol (5 ml) was acidified with a solution of HCl in diethyl ether. After evaporation of the acid solution to dryness, the solid obtained (120 mg) was crystallized from 10:1 ethyl acetate/methanol (22 ml) to give, after drying under the standard conditions, Ijw.HCl.1.25$H_2O$ (60 mg, 16% overall yield) in the form of a white solid, m.p. 220° C. (ethyl acetate/methanol) (dec.); IR (KBr) v: 3700–2000 (maxima at 3338 and 3179, NH, OH and $NH^+$ st), 1658 and 1587 (ar—C—C and ar—C—N st) $cm^{-1}$. The elemental analysis was in agreement with $C_{19}H_{22}N_2O$.HCl.1.25$H_2O$.

Example 17

12-Amino-6,7,10,11-tetrahydro-9-methyl-7,11-methanocycloocta[b]quinolin-13-one, Ikw.

This reaction was performed in a manner similar to that described for the preparation of Iaw, starting from $AlCl_3$ (0.81 g, 5.94 mmol), 2-aminobenzonitrile (0.70 g, 5.93 mmol), 1,2-dichloroethane (20 ml) and a solution of ketone IIk (490 mg, 2.98 mmol) in 1,2-dichloroethane (30 ml), and heating the reaction mixture to reflux for 4 h. The solid residue obtained (1.64 g) was subjected to column chromatography on silica gel using hexane/ethyl acetate/methanol mixtures of increasing polarity as eluent. On elution with 95:5 ethyl acetate/methanol, Ikw (0.46 g, 58% yield) was obtained.

12-Amino-6,7,10,11-tetrahydro-13,13-dihydroxy-9-methyl-7,11-methanocycloocta[b]quinoline hydrochloride (hydrochloride of the hydrated form corresponding to the ketone base), Ikw.HCl: A solution of Ikw (0.46 g) in dichloromethane (10 ml) was acidified with a solution of HCl in diethyl ether. After evaporation of the acid solution to dryness, the yellowish solid obtained (480 mg) was crystallized from 10:1 ethyl acetate/methanol (22 ml) to give, after drying under the standard conditions, Ikw.HCl.0.1$H_2O$ (230 mg, 24% overall yield) in the form of a white solid, m.p. 225° C. (ethyl acetate/methanol) (dec.); IR (KBr) v: 3700–2000 (maxima at 3355 and 3215, NH, OH and $NH^+$ st), 1651 and 1588 (ar—C—C and ar—C—N st) $cm^{-1}$. The elemental analysis was in agreement with $C_{17}H_{18}N_2O_2$.HCl.0.1$H_2O$.

Example 18

12-Amino-6,7,10,11-tetrahydro-9-methyl-7,11-[1](Z)-propenylidenocycloocta[b]quinoline, Ilw.

This reaction was performed in a manner similar to that described for the preparation of Iaw, starting from $AlCl_3$ (539 mg, 4.03 mmol), 2-aminobenzonitrile (476 mg, 4.03 mmol), 1,2-dichloroethane (45 ml) and a solution of ketone III (473 mg, 2.69 mmol) in 1,2-dichloroethane (9 ml), and heating the reaction mixture to reflux for 16 h. The semi-solid orange-coloured residue obtained (1.10 g) was subjected to column chromatography on silica gel (70 g) using hexane/ethyl acetate mixtures of increasing polarity as eluent. On elution with 1:1 hexane/ethyl acetate, Ilw (527 mg, 71% yield) was obtained.

Ilw.HCl: A solution of Ilw (527 mg) in methanol (25 ml) was acidified with a solution of HCl in diethyl ether. After evaporation of the acid solution to dryness, the orange-coloured solid obtained (645 mg) was crystallized from methanol (2.3 ml) to give, after drying under the standard conditions, Ilw.HCl.3/4$H_2O$ (263 mg, 30% overall yield) in the form of a white solid, m.p. 320° C. (methanol) (dec.); IR (KBr) v: 3700–2000 (maxima at 3334, 3188 and 2905, NH, OH and $NH^+$ st), 1640 and 1585 (ar—C—C and ar—C—N st) $cm^{-1}$. The elemental analysis was in agreement with $C_{19}H_{20}N_2.HCl.3/4H_2O$.

Example 19

12-Amino-6,7,10,11-tetrahydro-9-methyl-7,11-[1](E)-propenylidenocycloocta[b]quinoline, Imw.

This reaction was performed in a manner similar to that described for the preparation of Iaw, starting from $AlCl_3$ (682 mg, 5.11 mmol), 2-aminobenzonitrile (603 mg, 5.11 mmol), 1,2-dichloroethane (55 ml) and a solution of ketone IIm, heating the reaction mixture to reflux for 14 h. The semi-solid orange-coloured residue obtained (2.03 g) was subjected to column chromatography on silica gel (70 g) using hexane/ethyl acetate mixtures of increasing polarity as eluent. On elution with 1:1 hexane/ethyl acetate, Imw (740 mg, 79% yield) was obtained.

Imw.HCl: A solution of Imw (740 mg) in methanol (30 ml) was acidified with a solution of HCl in diethyl ether. After evaporation of the acid solution to dryness, the orange-coloured solid obtained (840 mg) was crystallized from methanol (2.5 ml) to give, after drying under the standard conditions, Imw.HCl (420 mg, 39% overall yield) in the form of a white solid, m.p. 250° C. (methanol) (dec.); IR (KBr) v: 3700–2000 (maxima at 3334, 3160 and 2905, NH and $NH^+$ st), 1652, 1627 and 1586 (ar—C—C and ar—C—N St) $cm^{-1}$. The elemental analysis was in agreement with $C_{19}H_{20}N_2.HCl$.

Example 20

12-Amino-6,7,10,11-tetrahydro-9-methyl-7,11-o-benzenocycloocta[b]quinoline, Inw.

This reaction was performed in a manner similar to that described for the preparation of Iaw, starting from $AlCl_3$ (125 mg, 0.94 mmol), aminobenzonitrile (111 mg, 0.94 mmol), 1,2-dichloroethane (20 ml) and a solution of ketone IIn (200 mg, 0.94 mmol) in 1,2-dichloroethane (10 ml), and heating the reaction mixture to reflux for 12 h. The yellowish solid residue obtained (240 mg) was subjected to column chromatography on silica gel (15 g) using hexane/ethyl acetate/methanol mixtures of increasing polarity as eluent. On elution with 90:10 ethyl acetate/methanol, Inw (210 mg, 71% yield) was obtained.

Inw.HCl: This was prepared from Inw (210 mg) in a manner similar to that described for Iaw.HCl. After evaporation of the acid solution to dryness, the dark solid obtained (215 mg) was crystallized from 1:1 ethyl acetate/methanol (10 ml) to give, after drying under the standard conditions, Inw.HCl.2.25$H_2O$ (160 mg, 44% overall yield) in the form of a white solid, m.p. 263–265° C. (ethyl acetate/methanol); IR (KBr) v: 3700–2000 (maxima at 3326 and 3218, NH, OH and $NH^+$ st), 1655, 1635 and 1583 (ar—C—C and ar—C—N st) $cm^{-1}$. The elemental analysis was in agreement with $C_{22}H_{20}N_2.HCl.2.25H_2O$.

Example 21

12-Amino-6,7,8,9,10,11-hexahydro-7,11-o-benzenocycloocta[b]quinoline, Iow.

This reaction was performed in a manner similar to that described for the preparation of Iaw, starting from $AlCl_3$ (2.00 g, 15.0 mmol), aminobenzonitrile (1.77 g, 15.0 mmol), 1,2-dichloroethane (120 ml) and a solution of ketone IIo (3.00 g, 15.0 mmol) in 1,2-dichloroethane (20 ml), and heating the reaction mixture to reflux for 12 h. The yellowish solid residue obtained (2.9 g) was subjected to column chromatography on silica gel (50 g) using hexane/ethyl acetate/methanol mixtures of increasing polarity as eluent. On elution with 90:10 ethyl acetate/methanol, Iow (1.25 g, 28% yield) was obtained.

Iow.HCl: This was prepared from Iow (1.25 g) in a manner similar to that described for Iaw.HCl. After evaporation of the acid solution to dryness, the dark solid obtained (1.3 g) was crystallized from 1:1 ethyl acetate/methanol (25 ml) to give, after drying under the standard conditions, Iow.HCl.2$H_2O$ (5.60 mg, 10% overall yield) in the form of a yellowish white solid, m.p. 120–122° C. (ethyl acetate/methanol) (dec.); IR (KBr) v: 3700–2000 (maxima at 3450, 3365 and 3250, NH, OH and $NH^+$ st), 1642 and 1570 (ar—C—C and ar—C—N st) $cm^{-1}$. The elemental analysis was in agreement with $C_{21}H_{20}N_2.HCl.2H_2O$.

Example 22

12-Amino-6,7,8,9,10,11-hexahydro-7,11-o-benzenocycloocta[b]quinolin-9-endo-ol, Iqw.

A solution was prepared of 12-amino-6,7,8,9,10,11-hexahydro-7,11-o-benzenocycloocta[b]quinolin-9-one (200 mg, 0.64 mmol) [Patent Application WO 93/13100] in methanol (30 ml), and $NaBH_4$ (100 mg, 2.7 mmol) was added portionwise. The reaction mixture was stirred at room temperature for 12 h, the solvent was evaporated off under reduced pressure and the resulting residue was suspended in 2N NaOH (30 ml). The mixture was heated at reflux for 30 min and filtered, washing the solid with water. After the solid was dried, the alcohol Iqw (175 mg, 87% yield) was obtained.

Iqw.HCl: This was prepared from Iqw (175 mg) in a manner similar to that described for Iaw.HCl. After evaporation of the acid solution to dryness, the dark solid obtained (197 mg) was crystallized from 1:1 ethyl acetate/methanol (10 ml) to give, after drying under the standard conditions, Iqw.HCl.2$H_2O$ (130 mg, 53% overall yield) in the form of a yellowish solid, m.p. 259–261° C. (ethyl acetate/methanol) (dec.); IR (KBr) v: 3700–2000 (maxima at 3374 and 3225, NH, OH and $NH^+$ st), 1637 and 1584 (ar—C—C and ar—C—N st) $cm^{-1}$. The elemental analysis was in agreement with $C_{21}H_{20}N_2O.HCl.2H_2O$.

Example 23

12-Amino-6,7,8,9,10,11-hexahydro-7,11-methanocycloocta[b]quinolin-9-endo-ol, Irw.

This reaction was performed in a manner similar to that described for the preparation of Iqw, starting from 12-amino-7,8,10,11-hexahydro-7,11-methano-6H-cycloocta

[b]quinolin-9-one (200 mg, 0.79 mmol) [Patent Application WO 93/13100], methanol (20 ml) and NaBH$_4$ (60 mg, 1.6 mmol), the impure alcohol Irw (180 mg) being obtained.

Irw.HCl: This was prepared from Irw (180 mg) in a manner similar to that described for Iaw.HCl. After evaporation of the acid solution to dryness, the brown solid obtained (200 mg) was crystallized from 1:1 ethyl acetate/methanol (12 ml) to give, after drying under the standard conditions, Irw.HCl.0.75H$_2$O (145 mg, 68% overall yield), m.p. 197–198° C. (ethyl acetate/methanol) (dec.); IR (KBr) v: 3700–2000 (maxima at 3515, 3463, 3338, 3251 and 3080, NH, OH and NH$^+$ st), 1659, 1575 and 1565 (ar—C—C and ar—C—N st) cm$^{-1}$. The elemental analysis was in agreement with C$_{16}$H$_{18}$N$_2$O.HCl.0.75H$_2$O.

Example 24

11-Amino-2,3,5,6,7,8,9,10-octahydro-6,10-methano-1H-cycloocta[e]cyclopenta[b]pyridin-8-endo-ol, Irz.

This reaction was performed in a manner similar to that described for the preparation of Iqw, starting from 11-amino-1,2,3,5,6,7,9,10-octahydro-6,10-methanocycloocta[e]cyclopenta[b]pyridin-8-one (500 mg, 2.06 mmol) [Patent Application WO 93/13100], methanol (50 ml) and NaBH$_4$ (150 mg, 3.96 mmol), the alcohol Irz (420 mg, 85% yield) being obtained.

Irz.HCl: This was prepared from Irz (420 mg) in a manner similar to that described for Iaw.HCl. After evaporation of the acid solution to dryness, the dark solid obtained (440 mg) was crystallized from 1:1 ethyl acetate/methanol (20 ml) to give, after drying under the standard conditions, Irz.HCl.2.5H$_2$O (330 mg, 50% overall yield), m.p. 162–164° C. (ethyl acetate/methanol) (dec.); IR (KBr) v: 3700–2000 (maxima at 3500 and 3417, NH, OH and NH$^+$ st), 1640 (ar—C—C and ar—C—N st) cm$^{-1}$. The elemental analysis was in agreement with C$_{15}$H$_{20}$N$_2$O.HCl.2.5H$_2$O.

Example 25

7-Ethylbicyclo[3.3.1]non-6-en-3-one, IIc.

a) 3-Ethyl-2-oxa-1-adamantanol, V (X=—CH$_2$—; R=—C$_2$H$_5$).

A solution of bicyclo[3.3.1]nonane-3,7-dione (1.00 g, 6.57 mmol) in anhydrous THF (100 ml) was added dropwise to a 22% solution, cooled in an ice bath, of ethylmagnesium chloride in THF (2.2 ml, 6.5 mmol). The reaction mixture was stirred for 3 h and was treated with 5% aqueous NH$_4$Cl solution until the white precipitate formed had dissolved completely (40 ml). The organic phase was separated and the aqueous phase was extracted with dichloromethane (3×100 ml). The combined organic extracts were dried with anhydrous Na$_2$SO$_4$ and evaporated under reduced pressure. On sublimation of the resulting solid residue (1.10 g) at 100° C./0.1 Torr, pure alcohol V (X=—CH$_2$—; R=—C$_2$H$_5$) (890 mg, 74% yield), m.p. 109–110.5° C. (sublimed) was obtained; IR (KBr) v: 3319 (OH st) cm$^{-1}$. The elemental analysis was in agreement with C$_{11}$H$_{18}$O$_2$.

b) 3-Ethyl-2-oxa-1-adamantile methanesulphonate, IV (X=—CH$_2$—; R=—C$_2$H$_5$).

A solution of alcohol V (X=—CH$_2$—; R=—C$_2$H$_5$) (5.47 g, 30.0 mmol) and anhydrous triethylamine (6.1 ml, 43.8 mmol) in anhydrous dichloromethane (150 ml) was prepared and cooled to −10° C. Methanesulphonyl chloride (3.6 ml, 31.2 mmol) was added dropwise, and the reaction mixture was stirred for 30 minutes and poured into a mixture of 10% aqueous HCl and crushed ice (100 ml). The organic phase was separated and the aqueous phase was washed with dichloromethane (3×200 ml). The combined organic extracts were washed with saturated aqueous NaHCO$_3$ solution (50 ml) and with brine (50 ml) and were dried with anhydrous Na$_2$SO$_4$. On evaporation of the solvent under reduced pressure, the mesylate IV (X=—CH$_2$—; R=—C$_2$H$_5$) (7.0 g, 89% yield) was obtained in the form of a white solid, m.p. 44–46° C. (dichloromethane); IR (KBr) v: 1356 and 1178 (S=O st) cm$^{-1}$. The elemental analysis was in agreement with C$_{12}$H$_{20}$O$_4$S.

c) 7-Ethylbicyclo[3.3.1]non-6-en-3-one, IIc.

A suspension of mesylate IV (X=—CH$_2$—; R=—C$_2$H$_5$) (7.31 g, 28.1 mmol) and silica-gel (7.5 g) in dichloromethane (75 ml) was stirred at room temperature for 3 hours and evaporated under reduced pressure, and the residue was subjected to column chromatography on silica gel (75 g) using hexane/ethyl acetate mixtures of increasing polarity as eluent. On elution with 80:20 hexane/ethyl acetate, the ketone IIc (1.94 g, 42% yield) was obtained in the form of an oil. Continuing the elution with 70:30 hexane/ethyl acetate, alcohol V (X=—CH$_2$—; R=—C$_2$H$_5$) (0.72 g, 14% yield) was obtained.

IIc: IR (NaCl) v: 1709 (C=O st) cm$^{-1}$. The elemental analysis was in agreement with C$_{11}$H16O.0.1H$_2$O.

Example 26

7-Propylbicyclo[3.3.1]non-6-en-3-one, IId.

a) 3-Propyl-2-oxa-1-adamantanol, V (X=—CH$_2$—; R=n—C$_3$H$_7$).

This reaction was performed in a manner similar to that described in the previous example, starting from a 2.0 M solution of propylmagnesium chloride in diethyl ether (74.0 ml, 147.8 mmol) and a solution of bicyclo[3.3.1]nonane-3,7-dione (15.0 g, 98.7 mmol) in anhydrous THF (300 ml), and stirring the reaction mixture for 30 min. On sublimation of the resulting semi-solid residue (18.8 g) at 80° C./0.5 Torr, pure alcohol V (X=—CH$_2$—; R=n—C$_3$H$_7$) (7.30 g, 38% yield), m.p. 66–67° C. (sublimed), was obtained; IR (KBr) v: 3317 (OH st) cm$^{-1}$. The elemental analysis was in agreement with C$_{12}$H$_{20}$O$_2$.

b) 3-Propyl-2-oxa-1-adamantile methanesulphonate, IV (X=—CH$_2$—; R=n—C$_3$H$_7$).

This reaction was performed in a manner similar to that described in the previous example, starting from 3-propyl-2-oxa-1-adamantanol V (X=—CH2—;, R=n—C$_3$H$_7$) (0.80 g, 4.08 mmol), anhydrous triethylamine (0.83 ml, 5.95 mmol), anhydrous dichloromethane (20 ml) and methanesulphonyl chloride (0.48 ml, 4.23 mmol), the mesylate IV (X=—CH$_2$—; R=n—C$_3$H$_7$) (1.02 g, 91% yield) being obtained in the form of an oil; IR (NaCl) v: 1357 and 1178 (S=O st) cm$^{-1}$. The elemental analysis was in agreement with C$_{13}$H$_{22}$O$_4$S.

c) 7-Propylbicyclo[3.3.1]non-6-en-3-one, IId.

This reaction was performed in a manner similar to that described for the preparation of IIc, starting from mesylate IV (X=—CH$_2$—; R=n—C$_3$H$_7$) (0.88 g, 3.21 mmol), silica gel (1 g) and dichloromethane (10 ml). The residue obtained was subjected to column chromatography on silica gel (9 g) using hexane/ethyl acetate mixtures of increasing polarity as eluent. On elution with 90:10 hexane/ethyl acetate, the ketone IId (0.27 g, 47% yield) was obtained. Continuing the elution with 70:30 hexane/ethyl acetate, alcohol V (X=—CH$_2$—; R=n—C$_3$H$_7$) (70 mg, 11% yield) was obtained.

IId: colourless oil, IR (NaCl) v: 1718 (C=O st) cm$^{-1}$. The elemental analysis was in agreement with C$_{12}$H$_{18}$O.

Example 27

7-Butylbicyclo[3.3.1]non-6-en-3-one. IIe.

a) 3-Butyl-2-oxa-1-adamantanol, V (X=—CH$_2$—; R=n—C$_4$H$_9$).

This reaction was performed in a manner similar to that described in Example 25, starting from a 1.6 M solution of n-butyllithium in hexane (70.0 ml, 112 mmol) and a solution of bicyclo[3.3.1]nonane-3,7-dione (10.0 g, 65.8 mmol) in anhydrous THF (200 ml), and stirring the reaction mixture for 30 min. On sublimation of the resulting solid residue (12.8 g) at 60° C./0.5 Torr, pure alcohol V (X=—CH$_2$—; R=n—C$_4$H$_9$) (8.95 g, 65% yield), m.p. 58–59° C. (sublimed), was obtained; IR (KBr) v: 3334 (OH st) cm$^{-1}$. The elemental analysis was in agreement with C$_{13}$H$_{22}$O$_2$.

b) 3-Butyl-2-oxa-1-adamantile methanesulphonate, IV (X=—CH$_2$—; R=n—C$_4$H$_9$).

This reaction was performed in a manner similar to that described for Example 25, starting from 3-butyl-2-oxa-1-adamantanol V (X=—CH$_2$—; R=n—C$_4$H$_9$) (8.83 g, 42.0 mmol), anhydrous triethylamine (8.5 ml, 61.0 mmol), anhydrous dichloromethane (210 ml) and methanesulphonyl chloride (5.0 ml, 63.0 mmol), the mesylate IV (X=—CH$_2$—; R=n—C$_4$H$_9$) (10.6 g, 88% yield) being obtained in the form of an oil; IR (NaCl) v: 1356 and 1177 (S=O st) cm$^{-1}$. For this compound, a satisfactory-elemental analysis could not be carried out.

c) 7-Butylbicyclo[3.3.1]non-6-en-3-one, IIe.

This reaction was performed in a manner similar to that described for the preparation of IIc, starting from mesylate IV (X=—CH$_2$—; R=n—C$_4$H$_9$) (13.6 g, 47.2 mmol), silica gel (14 g) and dichloromethane (140 ml). The residue obtained was subjected to column chromatography on silica gel (120 g) using hexane/ethyl acetate mixtures of increasing polarity as eluent. On elution with 95:5 hexane/ethyl acetate, the ketone IIe (3.7 g, 41% yield) was obtained. Continuing the elution with 90:10 hexane/ethyl acetate, alcohol V (X=—CH$_2$—; R=n—C$_4$H$_9$) (2.8 g, 28% yield) was obtained.

IIe: colourless oil, IR (NaCl) v: 1718 (C=O st) cm$^{-1}$. The elemental analysis was in agreement with C$_{13}$H$_{20}$O.0.1H$_2$O.

Example 28 syn-7,9-Dimethyl-9-methoxybicyclo[3.3.1]non-6-en-3-one, IIi, and anti-7,9-dimethyl-9-methoxybicyclo[3.3.1]non-6-en-3-one, IIj.

a) 9-Methyl-9-methoxybicyclo[3.3.1]nonane-3,7-dione, VI (X=—C—(CH$_3$) (OCH$_3$) —).

A solution was prepared of sodium (40 mg, 1.73 mmol) in methanol (30 ml), and a solution of 4-methyl-4-methoxy-2,5-cyclohexadienone (2.4 g, 17.4 mmol) in methanol (60 ml) and a solution of dimethyl acetonedicarboxylate (6.1 g, 35.0 mmol) in methanol (60 ml) were added dropwise. The reaction mixture was heated to reflux for 48 h and allowed to cool. Water (80 ml) and NaOH (2.0 g, 50.0 mmol) were added, the mixture was heated to reflux for 8 h and the organic solvent was evaporated off under reduced pressure. The resulting aqueous phase was acidified with 2 N HCl (30 ml), stirred for 1 h and extracted with dichloromethane (4×50 ml). The combined organic extracts were dried with anhydrous Na$_2$SO$_4$ and evaporated under reduced pressure. On sublimation of the resulting solid residue (3.00 g) at 110° C./1 Torr, pure VI (X=—C(CH$_3$)(OCH$_3$)—) (2.73 g, 81% yield) was obtained in the form of a white solid, m.p. 144° C. (dichloromethane); IR (KBr) v: 1714 (C=O st) cm$^{-1}$. The elemental analysis was in agreement with C$_{11}$H$_{16}$O$_3$.

b) syn-3,6-Dimethyl-6-methoxy-2-oxa-1-adamantanol, V (X=—C(CH$_3$) (syn-OCH$_3$)—; R=—CH$_3$), and anti-3,6-dimethyl-6-methoxy-2-oxa-1-adamantanol, V (X=—C (CH$_3$) (anti-OCH$_3$)—; R=—CH$_3$).

This reaction was performed in a manner similar to that described in Example 25, starting from a 22% solution of methylmagnesium chloride in THF (3.0 ml, 8.82 mmol) and a solution of 9-methyl-9-methoxybicyclo[3.3.1]nonane-3,7-dione VI (110 g, 5.61 mmol) in anhydrous THF (60 ml), and stirring the reaction mixture for 30 min, an oily crude product consisting of a mixture of syn and anti alcohols (1.05 g, 88% yield) in the approximate proportion 3:4 being obtained. On crystallization of this crude product with diethyl ether, pure V (X=—C(CH$_3$)(syn-OCH$_3$)—; R=—CH$_3$) (430 mg, 36% yield) was obtained in the form of a white solid. The crystallization mother liquors were subjected to column chromatography on silica gel using hexane/ethyl acetate mixtures of increasing polarity as eluent. On elution with 80:20 hexane/ethyl acetate, pure V (X=—C (CH$_3$)(anti-OCH$_3$)—; R=—CH$_3$) (217 mg, 18% yield) was obtained in the form of an oil.

V (X=—C(CH$_3$)(syn-OCH$_3$)—; R=—CH$_3$): m.p. 124–126° C. (diethyl ether); IR (KBr) v: 3361 (OH st) cm$^{-1}$. The elemental analysis was in agreement with C$_{12}$H$_{20}$O$_3$.

V (X=—C(CH$_3$)(anti-OCH$_3$)—; R=—CH$_3$): IR (NaCl) v: 3318 (OH St) cm$^{-1}$. The elemental analysis was in agreement with C$_{12}$H$_{20}$O$_3$.1/4H$_2$O.

c.1) syn-3,6-Dimethyl-6-methoxy-2-oxa-1-adamantile methanesulphonate, IV (X=—C(CH$_3$) (syn-OCH$_3$) —; R=—CH$_3$).

This reaction was performed in a manner similar to that described in Example 25, starting from alcohol V (X=—C (CH$_3$) (syn-OCH$_3$)—; R=—CH$_3$) (530 mg, 2.50 mmol), anhydrous triethylamine (0.69 ml, 4.95 mmol), anhydrous dichloromethane (15 ml) and methanesulphonyl chloride (0.38 ml, 4.89 mmol), the mesylate IV (X=—C(CH$_3$)(syn-OCH$_3$)—; R=—CH$_3$) (630 mg, 87% yield) being obtained in the form of a brown oil; IR (NaCl) v: 1368 and 1173 (S=O st) cm$^{-1}$. For this compound, a satisfactory elemental analysis could not be carried out.

d.1) syn-7,9-Dimethyl-9-methoxybicyclo[3.3.1]non-6-en-3-one, IIi.

A suspension of mesylate IV (X=—C(CH$_3$)(syn-OCH$_3$)—; R=—CH$_3$) (630 mg, 2.17 mmol) and silica gel (6 g) in dichloromethane (50 ml) was stirred at room temperature for 8 h. The mixture was filtered, washing with dichloromethane (3×50 ml) and with methanol (50 ml), and the combined filtrate and washings were evaporated under reduced pressure. The oily residue obtained (550 mg) was subjected to column chromatography on silica gel using hexane/ethyl acetate mixtures of increasing polarity as eluent. On elution with 90:10 hexane/ethyl acetate, the ketone IIi (190 mg, 45% yield) was obtained. Continuing the elution with 80:20 hexane/ethyl acetate, alcohol V (X=—C (CH$_3$)(syn-OCH$_3$)—; R=—CH$_3$) (120 mg, 26% yield) was obtained.

IIi: white solid, m.p. 37–38° C. (sublimed at 100° C./1.5 Torr; IR (KBr) v: 1711 (C=O st) cm$^{-1}$. The elemental analysis was in agreement with C$_{12}$H$_{18}$O$_2$.

c.2) anti-3,6-Dimethyl-6-methoxy-2-oxa-1-adamantile methanesulphonate, IV (X=—C(CH$_3$) (anti-OCH$_3$) —; R=—CH$_3$).

This reaction was performed in a manner similar to that described in Example 25, starting from alcohol V (X=—C (CH$_3$)(anti-OCH$_3$)—; R=—CH$_3$) (560 mg, 2.64 mmol), anhydrous triethylamine (0.73 ml, 5.23 mmol), anhydrous dichloromethane (15 ml) and methanesulphonyl chloride (0.41 ml, 5.30 mmol), the mesylate IV (X=—C(CH$_3$)(anti-OCH$_3$)—; R=—CH$_3$) (680 mg, 89% yield) being obtained in the form of a brown oil; IR (NaCl) v: 1369 and 1173 (S=O st) cm$^{-1}$. The elemental analysis was in agreement with C$_{13}$H$_{22}$O$_5$S.

d.2) anti-7,9-Dimethyl-9-methoxybicyclo[3.3.1]non-6-en-3-one, IIj.

This reaction was performed in a manner similar to that described for the preparation of IIi, starting from mesylate IV (X=—C(CH$_3$)(anti-OCH$_3$)—; R=—CH$_3$) (680 mg, 2.34 mmol), silica gel (6 g) and dichloromethane (50 ml), and stirring the mixture for 36 h. The oily residue obtained (590 mg) was subjected to column chromatography on silica gel using hexane/ethyl acetate mixtures of increasing polarity as eluent. On elution with 90:10 hexane/ethyl acetate, the ketone IIj (100 mg, 22% yield) was obtained. Continuing the elution with 50:50 hexane/ethyl acetate, alcohol V (X=—C(CH$_3$) (anti-OCH$_3$)—; R=—CH$_3$) (300 mg, 60% yield) was obtained.

IIj: colourless oil, IR (NaCl) v: 1713 (C=O st) cm$^{-1}$. The elemental analysis was in agreement with C$_{12}$H$_{18}$O$_2$.

Example 29

7-Methylbicyclo[3.3.1]non-6-ene-3,9-dione, IIk.

a) 3-Methyl-6,6-dimethoxy-2-oxa-1-adamantanol, V (X=—C(OCH$_3$)$_2$—; R=—CH$_3$).

This reaction was performed in a manner similar to that described in Example 25, starting from a 22% solution of methylmagnesium chloride in THF (2.91 ml, 8.55 mmol) and a solution of 6,6-dimethoxybicyclo[3.3.1]-nonane-3,7-dione (1.21 g, 5.70 mmol) in anhydrous THF (50 ml), and stirring the reaction mixture for 30 min. On crystallization of the resulting solid residue (900 mg) in diethyl ether, pure alcohol V (X=—C(OCH$_3$)$_2$—; R=—CH$_3$) (690 mg, 53% yield) was obtained in the form of a white solid, m.p. 132° C. (diethyl ether); IR (KBr) v: 3327 (OH st) cm$^{-1}$. The elemental analysis was in agreement with C$_{12}$H$_{20}$O$_4$.

b) 3-Methyl-6,6-dimethoxy-2-oxa-1-adamantile methanesulphonate, IV (X=—C(OCH$_3$)$_2$—; R=—CH$_3$).

This reaction was performed in a manner similar to that described in Example 25, starting from alcohol V (X=—C(OCH$_3$)$_2$—; R=—CH$_3$) (440 mg, 1.92 mmol), anhydrous triethylamine (0.40 ml, 2.9 mmol), anhydrous dichloromethane (10 ml) and methanesulphonyl chloride (0.22 ml, 2.8 mmol), the mesylate IV (X=—C(OCH$_3$)$_2$—; R=—CH$_3$) (580 mg, 98% yield) being obtained in the form of a colourless oil; IR (NaCl) v: 1359 and 1173 (S=O st) cm$^{-1}$. The elemental analysis was in agreement with C$_{13}$H$_{22}$O$_6$S.

c) 3-Methyl-2-oxa-6-oxo-1-adamantanol, V (X=—CO—; R=—CH$_3$) and 7-methylbicyclo[3.3.1]non-6-ene-3,9-dione, IIk.

A mixture of alcohol V (X=—C(OCH$_3$)$_2$—; R=—CH$_3$) (4.79 g, 21.0 mmol) and P$_2$O$_5$ (40.0 g, 282 mmol) in dichloromethane (200 ml) was heated to reflux for 8 h. The resulting suspension was filtered and the filtrate was evaporated under reduced pressure, a dark oil (4.14 g) being obtained. The solid filtration residue was dissolved in water and the solution was extracted with dichloromethane (4×40 ml). On evaporation of the combined organic extracts, a dark oil (330 mg) was obtained, which was combined with the above crude product and subjected to column chromatography on silica gel using hexane/ethyl acetate mixtures of increasing polarity as eluent, ketone IIk (690 mg, 20% yield) and alcohol V (X=—CO—; R=—CH$_3$) (1.41 g, 27% yield) being obtained.

IIk: m.p. 66–67° C. (sublimed at 60° C./0.5 Torr); IR (NaCl) v: 1731 and 1710 (C=O st) cm$^{-1}$. The elemental analysis was in agreement with C$_{10}$H$_{12}$O$_2$.

V (X=—CO—; R=—CH$_3$): m.p. 136–139° C. (diethyl ether); IR (KBr) v: 3334 (OH st) and 1727 (C=O st) cm$^{-1}$. The elemental analysis was in agreement with C$_{10}$H$_{14}$O$_3$.

d) 3-Methyl-2-oxa-6-oxo-1-adamantile methanesulphonate, IV (X=—CO—; R=—CH$_3$).

This reaction was performed in a manner similar to that described in Example 25, starting from alcohol V (X=—CO—; R=—CH$_3$) (1.19 g, 6.53 mmol), anhydrous triethylamine (1.36 ml, 9.80 mmol), anhydrous dichloromethane (33 ml) and methanesulphonyl chloride (0.76 ml, 9.80 mmol), the mesylate IV (X=—CO—; R=—CH$_3$) (1.64 g, 96% yield) being obtained in the form of a yellowish solid, m.p. 106–107° C. (diethyl ether); IR (KBr) v: 1732 (C=O st), 1358 and 1183 (S=O st) cm$^{-1}$. The elemental analysis was in agreement with C$_{11}$H$_{16}$O$_5$S.

e) 7-Methylbicyclo[3.3.1]non-6-ene-3,9-dione, IIk.

A solution of mesylate IV (X=—CO—; R=—CH$_3$) (400 mg, 1.53 mmol) and H$_2$SO$_4$ (0.2 ml, 2.0 mmol) in dichloromethane (10 ml) was stirred at room temperature for 4 days. The resulting mixture was washed with water (2×15 ml), dried with anhydrous Na$_2$SO$_4$ and evaporated under reduced pressure. On distillation of the resulting brown oil (250 mg) at 125° C./1 Torr, the ketone IIk (60 mg, 24% yield) was obtained.

Example 30

(E)-9-Ethylidene-7-methylbicyclo[3.3.1]non-6-en-3-one, III.

a) (Z)-9-Ethylidene-3-methyl-7-oxobicyclo[3.3.1]non-3-ene-1-carboxylic acid, VIII (R=H; R'=Me).

A mixture of methyl (Z)-7,7-ethylenedioxy-9-ethylidene-3-methylbicyclo[3.3.1]non-3-ene-1-carboxylate VII (R=H; R'=Me) (4.33 g, 15.6 mmol) [A. P. Kozikowski et al., Heterocycles 39, 101–116 (1994)], 20% aqueous NaOH solution (325 ml, 1.63 mol), THF (325 ml) and methanol (325 ml) was heated to reflux for 48 h under argon. The organic solvent was evaporated off under reduced pressure, and the resulting aqueous phase was washed with dichloromethane (2×50 ml), acidified with concentrated HCl and extracted with dichloromethane (3×100 ml). The combined organic extracts were washed with brine (100 ml) and dried with anhydrous Na$_2$SO$_4$. On evaporation of the solvent under reduced pressure, a gelatinous yellow residue (3.38 g) was obtained, which was dissolved in dioxane (40 ml) and treated with 2 N HCl (40 ml) at room temperature for 4 h. The resulting mixture was concentrated under reduced pressure, diluted with water (50 ml) and extracted with dichloromethane (3×30 ml). The combined organic extracts were washed with brine (50 ml) and dried with anhydrous Na$_2$SO$_4$. On evaporation of the solvent under reduced pressure, the acid VIII (R=H; R'=Me) (2.92 g, 85% yield) was obtained in the form of a yellowish solid, m.p. 134–136° C. (ethanol); IR (KBr) v: 2972 (COO—H st), 1724 (C=O st) cm$^{-1}$. The elemental analysis was in agreement with C$_{13}$H$_{16}$O$_3$.

b) (E)-9-Ethylidene-7-methylbicyclo[3.3.1]non-6-en-3-one, III.

A suspension of acid VIII (R=H; R'=Me) (1.25 g, 5.68 mmol) and thionyl chloride (1.65 ml, 20.4 mmol) in anhydrous toluene (185 ml) was heated to 80° C. for 4 h and concentrated under reduced pressure. The resulting residue was dissolved in anhydrous toluene (15 ml) and evaporated twice under reduced pressure to remove the thionyl chloride, an oily yellow residue (1.35 g) being obtained. Separately, a suspension of 2-thiopyridone N-oxide sodium salt (1.13 g, 7.58 mmol), 4-dimethylaminopyridine (75.5 mg, 0.62 mmol) and tert-butyl mercaptan (3.44 ml, 30.6 mmol) in anhydrous toluene (60 ml) was heated to reflux, and a solution of the above acid chloride in anhydrous toluene (30 ml) was added over 15 min. The reaction mixture was heated to reflux for 14 h, washed with water (2×30 ml) and with brine (30 ml) and dried with anhydrous Na$_2$SO$_4$. On evaporation of the solvent under reduced pressure, an oily brown residue (2.22 g) was obtained, which was dissolved in hexane (15 ml), washed with 3 N HCl (3×2.5 ml) and dried with anhydrous Na$_2$SO$_4$. On evaporation of the solvent under reduced pressure, an orange-coloured oil (1.15 g) was obtained, which was chromatographed on a column of silica gel (75 g) using a 99:1 hexane/ethyl acetate mixture as eluent, pure ketone III (770 mg, 77% yield) being obtained in the form of a colourless oil; IR (CHCl$_3$) v: 1706 (C=O st) cm$^{-1}$. The elemental analysis was in agreement with C$_{12}$H$_{16}$O.

Example 31

(Z)-9-Ethylidene-7-methylbicyclo[3.3.1]non-6-en-3-one, IIm.

This reaction was performed in a manner similar to that described for the preparation of III, starting from acid VIII (R=Me; R'=H) (1.00 g, 4.54 mmol) [A. P. Kozikowski et al., Heterocycles 39, 101–116 (1994)], thionyl chloride (1.10 ml, 13.6 mmol) and anhydrous toluene (150 ml) for the preparation of the acid chloride, and from 2-thiopyridone N-oxide (0.82 g, 5.50 mmol), 4-dimethylaminopyridine (55.0 mg, 0.45 mmol), tert-butyl mercaptan (2.50 ml, 22.2 mmol) and anhydrous toluene (50 ml), and heating to reflux for 4 h in order to effect decarboxylation. The oily brown residue obtained (1.34 g) was dissolved in hexane (15 ml), washed with 3 N HCl (3×2.5 ml) and dried with anhydrous Na$_2$SO$_4$. On evaporation of the solvent under reduced pressure, the ketone IIm (614 mg, 77% yield) was obtained in the form of a colourless oil. The acid washing liquors were combined and extracted with toluene (2×10 ml) and with hexane (3×10 ml). The combined organic extracts were evaporated, and the residue obtained (419 mg) was dissolved in hexane (10 ml), washed with 2 N HCl (8×2 ml) and evaporated under reduced pressure, more ketone IIm (35 mg, 4% of 81% overall yield) being obtained; IR (KBr) v: 1705 (C=O st) cm$^{-1}$. The elemental analysis was in agreement with C$_{12}$H$_{16}$O.

Example 32

5,6,8,9-Tetrahydro-11-methyl-5,9-[1]propeno-5H-benzocyclohepten-7-one, IIn.

a) 11,11-Ethylenedioxy-6,7,8,9-tetrahydro-7-exo-methyl-5,9-propano-5H-benzocyclohepten-7-endo-ol, X.

This reaction was performed in a manner similar to that described in Example 25, starting from a 5% solution of methyllithium in diethyl ether (15 ml, 24.0 mmol) and a solution of 11,11-ethylenedioxy-6,7,8,9-tetrahydro-5,9-propano-5H-benzocyclohepten-7-one IX (2.00 g, 7.74 mmol) in anhydrous THF (25 ml). On crystallization of the resulting solid residue (1.90 g, 89% yield) in chloroform (15 ml), pure alcohol X (1.20 g, 56% yield) was obtained in the form of a white solid, m.p. 146–148° C. (chloroform) : IR (KBr) v: 3462 (OH st) cm$^{-1}$. The elemental analysis was in agreement with C$_{17}$H$_{22}$O$_3$.

b) 5,6,8,9-Tetrahydro-11-methyl-5,9-[1]propeno-5H-benzocyclohepten-7-one, IIn.

Methanesulphonyl chloride (0.5 ml, 6.45 mmol) was added dropwise to a mixture of alcohol X (1.20 g, 4.37 mmol) and anhydrous pyridine (10 ml) at 0° C. The reaction mixture was stirred for 3 h and poured into a mixture of 2 N HCl (60 ml) and crushed ice (20 ml). The organic phase was separated, washed with saturated aqueous NaHCO$_3$ solution (60 ml) and with brine (60 ml) and dried with anhydrous Na$_2$SO$_4$. On evaporation of the solvent under reduced pressure, a residue (1.5 g) was obtained, which was subjected to column chromatography on silica gel (50 g) using hexane/ethyl acetate mixtures of increasing polarity as eluent. On elution with 80:20 hexane/ethyl acetate, the ketone IIn (320 mg, 34% yield) was obtained in the form of a colourless oil; IR (NaCl) v: 1695 (C=O set) cm$^{-1}$. The elemental analysis was in agreement with C$_{15}$H$_{16}$O.

Example 33

Obtaining of (−)-7-ethylbicyclo[3.3.1]non-6-en-3-one, (−)—IIc.

a) (−)-7,7-Ethylenedioxy-3-(trifluoromethylsulphonyloxy) bicyclo[3.3.1]non-2-ene, (−)-XII (X=CH$_2$).

(+)-Bis[(R)-1-phenylethyl]amine [2.76 g, 12.2 mmol, $[\alpha]^{20}_D$=+165 (c=1.10, CHCl$_3$)] and anhydrous tetrahydrofuran (THF) (110 ml) were placed in a 250-ml three-necked round-bottomed flask provided with an internal thermometer, inert atmosphere and magnetic stirrer. The solution was cooled to −78° C. in an acetone/CO$_2$ bath, a 1.6 M solution of n-butyllithium in hexane (7.65 ml, 12.2 mmol) was added dropwise, and the mixture was stirred at this temperature for 5 min and subsequently allowed to warm up to room temperature over 1 h. The solution was cooled again to −78° C., a solution of lithium chloride (87.0 mg, 2.04 mmol) in anhydrous THF (9.50 ml) was added dropwise (2 min), and a solution of the ketone XI (X=CH$_2$) (2.0 g, 10.2 mmol) in anhydrous THF (12 ml) was then added dropwise. The mixture was stirred at this temperature for 15 min, and a solution of N-phenylbis(trifluoromethylsulphonyl)imide (5.46 g, 15.3 mmol) in anhydrous THF (10 ml) was thereafter added dropwise (10 min) . The reaction mixture was stirred at room temperature for 16 h and concentrated under reduced pressure to an approximate volume of 10 ml, and ethyl acetate (10 ml), hexane (220 ml) and water (50 ml) were added. The aqueous phase was separated after settling had taken place, and the organic phase was washed successively with 2 N aqueous sodium hydroxide solution (2×50 ml), 2 N aqueous hydrochloric acid solution (2×50 ml) and water (2×55 ml), dried with anhydrous sodium sulphate and filtered. On evaporation of the solvent under reduced pressure, a yellow residue (4.08 g) was obtained, which was chromatographed on a column of silica gel (60–200 μm, 150 g), eluting with a 97.5:2.5 hexane/ethyl acetate mixture, (−)-XII (X=CH$_2$) (2.15 g, 64% yield), b.p. 65° C./1 Torr, $[\alpha]^{20}_D$=−45.6 (c=1.02, CHCl$_3$), ee=81%, being obtained.

$^1$H NMR (500 MHz, CDCl$_3$), δ: 1.61 (dt, J=12.5 Hz, J'=3.0 Hz, 1H, 9-H$_{anti}$), 1.72 (dm, J=12.5 Hz, 1H, 9-H$_{syn}$), 1.77 (dd, J=14.0 Hz, J'=4.5 Hz, 1H, 8-H$_{exo}$) 1.80–1.85 (complex abs., 3H, 8-H$_{endo}$, 6-H$_{exo}$ and 6-H$_{endo}$), 2.27 (d, J=17.5 Hz, 1H, 4-H$_{endo}$), 2.43 (m, 1H, 5-H), 2.57 (dd, J=17.5 Hz, J'=7.5 Hz, 1H, 4-H$_{exo}$), 2.65 (broad s, 1H, 1-H), 3.78 (m, 2H) and 3.91 (m, 2H) (O—CH$_2$—CH$_2$—O), 5.76 (d, J=6.5 Hz, 1H, 2-H).

$^{13}$C NMR (75.4 MHz, CDCl$_3$), δ: 28.2 (CH, C5), 29.2 (CH, Cl), 30.0 (CH$_2$, C9), 33.3 (CH$_2$, C4), 38.0 (CH$_2$, C8), 41.5 (CH$_2$, C6), 63.1 and 64.8 (CH$_2$, O—CH$_2$—CH$_2$—O), 107.7 (C, C7), 118.5 (C, q, J=320 Hz, CF$_3$), 120.9 (CH, C2), 149.8 (C, C3).

IR (CHCl$_3$), v: 2928, 1414, 1244, 1143, 1092, 1075, 1050, 1024, 978, 964, 875 cm$^{-1}$.

The elemental analysis was in agreement with C$_{12}$H$_{15}$F$_3$O$_5$S.

b) (−)-7,7-Ethylenedioxy-3-ethylbicyclo[3.3.1]non-2-ene, (−)-XIII (X=CH$_2$, R=CH$_2$CH$_3$).

CuBr.Me$_2$S complex (4.71 g, 22.9 mmol) and anhydrous THF (20 ml) were placed in a 250-ml three-necked round-bottomed flask provided with an inert atmosphere and magnetic stirrer. The greyish suspension was cooled to −78° C. in an acetone/CO$_2$ bath, and a 1 M solution of ethylmagnesium bromide in anhydrous THF (41.1 ml, 41.1 mmol) was added dropwise. The bath was removed and the mixture was stirred until it turned black (as the addition neared completion, a greyish paste formed which became fluid when the bath was removed). When about 15 min had elapsed, the mixture was cooled again to −78° C. and a solution of (−)-XII (X=CH$_2$) [1.50 g, 4.57 mmol, $[\alpha]^{20}_D$=−

45.6 (C=1.02, CHCl$_3$), ee=81%] in anhydrous THF (20 ml) was added. The black mixture was stirred at room temperature for 16 h, allowed to sediment for 10 min and filtered, washing the black solid residue with hexane (35 ml). On evaporation of the solvent from the filtrate under reduced pressure, a gelatinous yellowish residue (1.05 g) was obtained, which was chromatographed through neutral alumina (300 g), eluting with a 98:2 hexane/ethyl acetate mixture, (−)-XIII (X=CH$_2$, R=CH$_2$CH$_3$) being obtained in the form of a yellowish oil (616 mg). The analytical sample was obtained by distillation under reduced pressure, b.p. 60° C./0.5 Torr, [α]$^{20}_D$=−82.6 (c=1.08, CHCl$_3$).

$^1$H NMR (500 MHz, CDCl$_3$), δ: 0.97 (t, J=7.5 Hz, 3H CH$_2$—CH$_3$), 1.55 (broad d, J=12.0 Hz, 1H, 9-H$_{anti}$), 1.65 (broad d, J=12.0 Hz, 1H, 9-H$_{syn}$), 1.73 (m, 2H, 8-H$_{exo}$ and 8-H$_{endo}$), 1.76 (m, 2H, 6-H$_{exo}$ and 6-H$_{endo}$), 1.88 (d, J=17.0 Hz, 1H, 4-H$_{endo}$), 1.93 (m, 2H, CH$_2$—CH$_3$), 2.21 (complex abs., 1H, 4-H$_{exo}$), 2.23 (broad s, 1H, 5-H), 2.38 (broad s, 1H, 1-H), 3.71–3.97 (complex abs., 4H, O—CH$_2$—CH$_2$—O), 5.44 (dm, J=6.5 Hz, 1H, 2-H).

$^{13}$C NMR (75.4 MHz, CDCl$_3$), δ: 12.3 (CH$_3$, CH$_2$—CH$_3$), 27.6 (CH, C5), 29.1 (CH, C1), 30.1 (CH$_2$, CH$_2$—CH$_3$), 31.2 (CH$_2$, C9), 34.4 (CH$_2$, C4), 39.1 (CH$_2$, C8), 41.7 (CH$_2$, C6), 62.7 and 64.4 (CH$_2$, O—CH$_2$—CH$_2$—O), 109.0 (C, C7), 122.6 (CH, C2), 139.6 (C, C3).

IR (CHCl$_3$), ν: 2925, 1453, 1428, 1365, 1263, 1245, 1227, 1190, 1143, 1081, 1022, 947, 860 cm$^{-1}$.

The elemental analysis was in agreement with C$_{13}$H$_{20}$O$_2$.

c) (−)-7-Ethylbicyclo[3.3.1]non-6-en-3-one, (−)-IIc.

(−)-XIII (X=CH$_2$, R=CH$_2$CH$_3$) [494 mg, 3.37 mmol, [α]$^{20}_D$=−82.6 (c=1.08, CHCl$_3$)], silica gel (40–60 μm, 4.5 g) and CH$_2$Cl$_2$ (15 ml) were placed in a 50-ml one-necked round-bottomed flask provided with a magnetic stirrer, and the mixture was stirred at room temperature for 27 h, the solvent was evaporated off under reduced pressure and the residue was subjected to column chromatography on silica gel (60–200 μm, 15 g), eluting with a 97:3 mixture of hexane and ethyl acetate, (−)-II (X=CH$_2$, R=CH$_2$CH$_3$) [179 mg, 30% yield based on (−)-XII (X=CH$_2$)], b.p. 45° C./0.4 Torr, [α]$^{20}_D$=−85 (c=0.93, CHCl$_3$), ee=81%, being obtained.

$^1$H NMR (500 MHz, CDCl$_3$), δ: 0.92 (t, J=7.5 Hz, 3H CH$_2$—CH$_3$), 1.80 (broad d, J=18.0 Hz, 1H, 8-H$_{endo}$), 1.86 (broad q, J=7.5 Hz, 2H, CH$_2$—CH$_3$), 1.92 (dm, J=12.5 Hz, 1H, 9-H$_{anti}$), 1.98 (dm, J=12.5 Hz, 1H, 9-H$_{syn}$), 2.23 (dq, J=15.5 Hz, J'=2.0 Hz, 1H, 2-H$_{endo}$), 2.29 (dq, J=14.5 Hz, J'=2.0 Hz, 1H, 4-H$_{endo}$), 2.33 (broad dd, J=18.0 Hz, J'=6.0 Hz, 1H, 8-H$_{exo}$), 2.41 (dd, J=14.5 Hz, J'=4.0 Hz, 1H, 4-H$_{exo}$) 2.47 (ddt, J=15.5 Hz, J'=6.5 Hz, J"=1.0 Hz, 1H, 2-H$_{exo}$), 2.56 (m, 1H, 1-H), 2.65 (broad s, 1H, 5-H), 5.40 (dm, J=6.0 Hz, 1H, 6-H).

$^{13}$C NMR (50.3 MHz, CDCl$_3$), δ: 12.3 (CH$_3$, CH$_2$—CH$_3$), 29.8 (CH$_2$, CH$_2$—CH$_3$), 30.2 (CH, C1), 30.5 (CH$_2$, C9), 30.9 (CH, C5), 35.7 (CH$_2$, C8), 46.7 (CH$_2$, C4), 49.1 (CH$_2$, C2), 123.0 (CH, C6), 138.3 (C, C7), 212.3 (C, C3).

IR (NaCl), ν: 1709 cm$^{-1}$.

The elemental analysis was in agreement with C$_{11}$H$_{16}$O.

Example 34

Obtaining of (+)-7-ethylbicyclo[3.3.1]non-6-en-3-one, (+)—IIc.

a) (+)-7,7-Ethylenedioxy-3-(trifluoromethylsulphonyloxy) bicyclo[3.3.1]non-2-ene, (+)-XII (X=CH$_2$).

(−)-Bis[(S)-1-phenylethyl]amine [2.07 g, 9.18 mmol, [α]$^{20}_D$=−167 (c=1.02, CHCl$_3$)] and anhydrous THF (80 ml) were placed in a 250-ml three-necked round-bottomed flask equipped with an internal thermometer, inert atmosphere and magnetic stirrer. The solution was cooled to −78° C. in an acetone/CO$_2$ bath, a 1.6 M solution of n-butyllithium in hexane (5.74 ml, 9.18 mmol) was added dropwise, and the mixture was stirred at this temperature for 5 min and then left at room temperature for 1 h. The solution was cooled again to −78° C., a solution of lithium chloride (65.0 mg, 1.53 mmol) in anhydrous THF (7.0 ml) was added dropwise (2 min), and a solution of XI (X=CH$_2$) (1.5 g, 7.65 mmol) in THF (9.0 ml) was then added dropwise (2 min). The mixture was stirred at this temperature for 15 min and a solution of N-phenylbis(trifluoromethylsulphonyl)imide (4.10 g, 11.5 mmol) in anhydrous THF (8 ml) was added dropwise (10 min). The reaction mixture was stirred at room temperature for 16 h and concentrated under reduced pressure to an approximate volume of 8 ml, ethyl acetate (5 ml), hexane (165 ml) and water (40 ml) were added and the aqueous phase was separated after settling had taken place. The organic phase was washed successively with 2 N aqueous sodium hydroxide solution (2×40 ml), 2 N aqueous hydrochloric acid solution (2×40 ml) and water (2×50 ml), dried with anhydrous sodium sulphate and filtered. On evaporation of the solvent under reduced pressure, a yellow residue was obtained which was a mixture of an oil and a crystalline solid (3.23 g), which was chromatographed on a column of silica gel (60–200 μm, 140 g), eluting with a 97.5:2.5 hexane/ethyl acetate mixture, (+)-XII (X=CH$_2$) being obtained in the form of a yellowish oil (1.99 g, 79% yield), b.p. 65° C./1 Torr, [α]$^{20}_D$=+43 (c=1.08, CHCl$_3$), ee=80%. The $^1$H and $^{13}$C NMR data coincide with those for (−)-XII (X=CH$_2$), and the elemental analysis was in agreement with C$_{12}$H$_{15}$F$_3$O$_5$S.

b) (+)-7,7-Ethylenedioxy-3-ethylbicyclo[3.3.1]non-2-ene, (+)-XIII (X=CH$_2$, R=CH$_2$CH$_3$).

CuBr.Me$_2$S complex (4.71 g, 22.9 mmol) and anhydrous THF (20 ml) were placed in a 250-ml three-necked round-bottomed flask provided with a thermometer, inert atmosphere and magnetic stirrer. The greyish suspension was cooled to −78° C. in an acetone/CO$_2$ bath, and a 1 M solution of ethylmagnesium bromide in THF (41.1 ml, 41.1 mmol) was added dropwise. The bath was removed and the mixture was stirred until it turned black (as the addition neared completion, a greyish paste formed which became fluid when the bath was removed). When 15 min had elapsed, the mixture was cooled again to −78° C. (resolidifying), and a solution of (+)-XII (X=CH$_2$) [1.50 g, 4.57 mmol, -[α]$^{20}_D$=+43 (c=1.08, CHCl$_3$), ee=80%] in anhydrous THF (20. ml) was added. The black mixture was stirred at room temperature for 16 h, allowed to sediment for 10 min and filtered, washing the black solid residue with hexane (30 ml). The filtrate was concentrated at low temperature and under reduced pressure to a volume of about 25 ml and filtered again, and the solvent was evaporated off from the filtrate under reduced pressure, a gelatinous yellowish residue (0.94 g) being obtained, which was chromatographed through neutral alumina (300 g), eluting with a 98:2 mixture of hexane and ethyl acetate, (+)-XIII (X=CH$_2$, R=CH$_2$CH$_3$) being obtained in the form of a yellowish oil (687 mg, 72% yield), b.p. 60° C./0.5 Torr, [α]$^{20}_D$=+87.2 (c=1.03, CHCl$_3$). The 1H and $^{13}$C NMR data coincide with those for (−)-XIII (X=CH$_2$, R=CH$_2$CH$_3$), and the elemental analysis was in agreement with C$_{13}$H$_{20}$O$_2$.

c) (+)-7-Ethylbicyclo[3.3.1]non-6-en-3-one, (+)-IIc (+)-XIII (X=CH$_2$, R=CH$_2$CH$_3$) [530 mg, 2.55 mmol, [α]$^{20}_D$=+87.2 (c=1.03, CHCl$_3$)], silica gel (40–60 μm, 6.5 g) and CH$_2$Cl$_2$ (15 ml) were placed in a 50-ml one-necked round-bottomed flask provided with a magnetic stirrer, and the mixture was stirred at room temperature for 27 h. The solvent was evaporated off under reduced pressure and the residue was chromatographed on a column of silica gel (60–200 μm, 15 g), eluting with a 97:3 mixture of hexane and ethyl acetate, (+)-IIc being obtained in the form of a yellowish oil (340 mg, 81% yield), b.p. 45° C./0.4 Torr, $[\alpha]^{20}_D$=+81 (c=0.96, CHCl$_3$), ee=80%.

The $^1$H and $^{13}$C NMR data coincide with those for (−)-IIc, and the elemental analysis was in agreement with C$_{11}$H$_{16}$O.

Example 35

(+)-12-Amino-6,7,10,11-tetrahydro-9-ethyl-7,11-methanocycloocteno[b]quinoline hydrochloride, (+)-Icw.HCl Anhydrous AlCl$_3$ (81.0 mg, 0.61 mmol), 2-aminobenzonitrile (54.0 mg, 0.46 mmol) and 1,2-dichloroethane (2.5 ml) were placed in a 25-ml 2-necked round-bottomed flask provided with a reflux condenser, inert atmosphere and magnetic stirrer. A solution of (−)-IIc [50 mg, 0.30 mmol, $[\alpha]^{20}_D$=−85 (c=0.93, CHCl$_3$), ee=81%] in 1,2-dichloroethane (0.75 ml) was thereafter added dropwise over 10 min, and the mixture was heated to reflux for 14 h. It was allowed to cool, water (2 ml) and THF (2 ml) were added, and the mixture was alkalinized with 5 N aqueous NaOH solution (1 ml) and stirred at room temperature for 30 min. It was concentrated under reduced pressure, and the resulting aqueous suspension containing a viscous orange-coloured solid was filtered, washing the residue with water (5 ml). The solid was dissolved in methanol (3 ml) and the solution was evaporated under reduced pressure, giving an orange-coloured waxy residue (105 mg) which was chromatographed on a column of silica gel (60–200 μm, 40 g), eluting first with hexane, hexane/ethyl acetate mixtures, ethyl acetate and finally ethyl acetate/methanol mixtures, (+)-Icw being obtained on elution with ethyl acetate/methanol mixtures (64 mg, 80% yield, ee=50%). (+)-Icw was converted to its hydrochloride by dissolution in methanol (2 ml) and addition of a 0.38 N solution of HCl in ethyl ether (3 ml). On evaporation of the solvent under reduced pressure, (+)-Icw.HCl (90 mg) was obtained.

(+)-Icw.HCl (544 mg, ee=53%) obtained by an operation similar to the one above was crystallized in ethyl acetate (5 ml) and methanol (2.5 ml), (+)-Icw.HCl (188 mg, ee=99%), $[\alpha]^{20}_D$=+353 (c=0.95, MeOH), m.p. 320° C. (with dec. beginning at 225° C.), being obtained. The $^1$H and $^{13}$C NMR data coincide with those for (±)-Icw. IR (KBr) v: 3328, 3178, 2880, 2819, 1667, 1650, 1638, 1585, 1496, 1463, 1412, 1373, 1183, 1158, 852, 771 cm$^{-1}$. The elemental analysis was in agreement with C$_{18}$H$_{20}$N$_2$.HCl.

Example 36

(−)-12-Amino-6,7,10,11-tetrahydro-9-ethyl-7,11-methanocycloocteno[b]quinoline hydrochloride, (−)-Icw.HCl This reaction was performed in a manner similar to that described in the previous example for (+)-Icw.HCl. Starting from anhydrous AlCl$_3$ (252 mg, 1.89 mmol), 2-aminobenzonitrile (168 mg, 1.42 mmol) and 1,2-dichloroethane (7 ml), and a solution of (+)-IIc [155 mg, 0.94 mmol, $[\alpha]^{20}_D$=+81 (c=0.96, CHCl$_3$), ee=81%] in 1,2-dichloroethane (1.5 ml), (−)-Icw (199 mg, 80% yield, ee=57%) was obtained.

On crystallization of (−)-Icw.HCl (242 mg, 22% ee), obtained by other operations like the one above in which the starting material had been a ketone (+)-IIc with a smaller enantiomeric excess, in ethyl acetate (5 ml) and methanol (2 ml), (−)-Icw.HCl (45 mg,>99% ee), $[\alpha]^{20}_D$=−345 (c=0.99, MeOH), m.p. 310° C. (with dec. beginning at 240° C.), was obtained. The $^1$H and $^{13}$C NMR data coincide with those for (±)-Icw. IR (KBr), v: 3329, 3180, 2930, 2886, 2821, 1672, 1650, 1628, 1585, 1494, 1461, 1412, 1373, 1184, 1162, 852, 763 cm$^{-1}$. The elemental analysis was in agreement with C$_{18}$H$_{20}$N$_2$.HCl.2/3H$_2$O.

Example 37

Chromatographic separation of the racemic mixture (±)-12-amino-6,7,10,11-tetrahydro-9-ethyl-7,11-methanocycloocteno[b]quinoline, (±)-Icw The chromatographic separation of (±)-Icw was carried out using a medium pressure liquid chromatography (MPLC) system consisting of a pump, a column with a chiral stationary phase and a UV detector. The chiral stationary phase is cellulose triacetate (Merck 16362) with a particle size of 15–25 μm. In the process, 4 introductions were carried out of (±) -Icw base, of 135 mg each time, using 96% ethanol as eluent, a flow rate of 1.8–2.0 ml/min and a pressure of 8–12 bar. Overall, (−)-Icw (269 mg) with an ee>90% and (+)-Icw (241 mg) with an ee>85% were obtained.

(−)-Icw (269 mg) was dissolved in MeOH (10 ml), and a 0.38 N solution of HCl in ethyl ether (8 ml) was added. The organic solvents were evaporated off under reduced pressure, (−)-Icw.HCl (307 mg) being obtained, which was crystallized in a mixture of ethyl acetate (3 ml) and methanol (2.2 ml), a brown crystalline solid corresponding to (−)-Icw.HCl (130 mg, 99% ee), $[\alpha]^{20}_D$=−345 (c=0.95 MeOH), being obtained.

(+)-Icw (241 mg) was dissolved in MeOH (8 ml), and a 0.38 N solution of HCl in ethyl ether (7 ml) was added. The organic solvents were evaporated off under reduced pressure, (+)-Icw.HCl (275 mg) being obtained, which was crystallized in a mixture of ethyl acetate (2.5 ml) and methanol (1.8 ml), a brown crystalline solid corresponding to (+)-Icw.HCl (85 mg,>99% ee), $[\alpha]^{20}_D$=+350 (c=0.99, MeOH), being obtained.

Note: The ee values were determined in both cases on a sample of the (+)- or (−)-Icw base liberated from its hydrochloride.

Example 38

Chromatographic separation of the racemic mixture (±)-12-amino-6,7,10,11-tetrahydro-9-methyl-7,11-methanocycloocteno[b]quinoline, (+)-Ibw The chromatographic separation of (±)-Ibw was carried out using the system described in Example 37. In the process, 4 introductions were carried out of (±)-Ibw in base form (1×100 mg+3×150 mg) using 96% ethanol as eluent, a flow rate of 2.0–2.5 ml/min and a pressure of 8–12 bar. Overall, (−)-Ibw (189 mg, ee>90%) and (+)-Ibw (140 mg, ee>80%) were obtained.

(−)-Ibw was dissolved in MeOH (10 ml), and a 0.38 N solution of HCl in ethyl ether (10 ml) was added. The organic solvents were evaporated off under reduced pressure, (−)-Ibw.HCl (264 mg) being obtained, which was dissolved in MeOH (0.25 ml), and ethyl acetate (1.5 ml) was added. The precipitate formed was filtered off, (−)-Ibw.HCl (124 mg, ee=90%) being obtained in the form of a pulverulent brown solid, m.p. 295° C. (with dec. beginning at 240° C.), $[\alpha]^{20}_D$=−328 (c=1.0, MeOH). The $^1$H and $^{13}$C NMR data coincide with those for (±)-Ibw. IR (KBr) v: 3338, 3182, 2918, 2874, 2852, 2811, 1666, 1650,1634, 1585, 1495, 1457, 1414, 1374, 1187, 1160, 874, 841, 764 cm$^{-1}$.

The elemental analysis was in agreement with C$_{17}$H$_{18}$N$_2$ HCl.1/2H$_2$O.

(+)-Ibw (140 mg, ee>80%) was dissolved in MeOH (7 ml), and a 0.38 N solution of HCl in ethyl ether (8 ml) was added. The organic solvents were evaporated off under reduced pressure, (+)-Ibw.HCl (201 mg) being obtained, which was dissolved in MeOH (0.20 ml), ethyl acetate (1.2 ml) was added and the precipitate formed was filtered off, (+)-Ibw.HCl (114 mg, ee=87%) being obtained in the form of a pulverulent brown solid, m.p. 300° C. (with dec.

beginning at 250° C.), $[\alpha]^{20}{}_D$=+309 (c=1.0, MeOH). The $^1$H and $^{13}$C NMR data coincide with those for (±)-Ibw. IR (KBr), ν: 3319, 3178, 2925, 2892, 2870, 2810, 1666, 1646, 1636, 1600, 1584, 1490, 1457, 1414, 1373, 1181, 1159, 878, 845, 768 cm$^{-1}$. The elemental analysis was in agreement with $C_{17}H_{18}N_2 \cdot HCl \cdot 2/3H_2O$.

Note: The ee values were determined in both cases on a sample of (+)- or (−)-Ibw base liberated from its hydrochloride.

Example 39

Acetylcholinesterase-inhibiting capacity

The capacity of the compounds obtained in Examples 1 to 24 and 35 to 38 for inhibiting acetylcholinesterase was determined using the colorimetric method described by Ellman et al., Biochem. Pharmacol., 7, 88–95 (1961).

All the compounds showed inhibitory activity against the enzyme acetylcholinesterase, and some of them activity plainly greater than that of tacrine. As can be seen, the two enantiomers of the same compound display significant differences in activity, the laevorotatory enantiomers (−)-Ibw and (−)-Icw being much more active than their enantiomers (+) -Ibw and (+) -Icw, respectively.

Table 8 shows the inhibitory activity against the enzyme of some of the compounds obtained, with respect to that shown by tacrine under the same conditions, expressed as the ratio of the $IC_{50}$ of tacrine (concentration which inhibits 50% of the enzyme) to the $IC_{50}$ of each compound.

TABLE 8

Acetylcholinesterase-inhibiting activity of the compounds Ibw, Ibx, Iby, Icw, Ifw, (+) —Ibw (87% ee), (−) —Ibw (90% ee), (+) —Icw (99% ee) and (−) —Icw (>99% ee) compared with tacrine

| Compound | $IC_{50}$ tacrine/$IC_{50}$ compound |
|---|---|
| Ibw | 2.00 |
| Ibx | 4.14 |
| Iby | 15.28 |
| Icw | 3.38 |
| Ifw | 1.03 |
| (+) —Ibw | 0.40 |
| (−) —Ibw | 2.80 |
| (+) —Icw | 0.15 |
| (−) —Icw | 4.80 |

We claim:

1. Polycyclic aminopyridine compounds of general Formula I

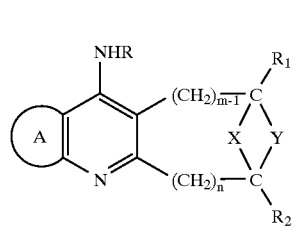

(I)

and their pharmaceutically acceptable salts, in which: R is hydrogen, alkyl, aralkyl, or acyl; $R_1$ and $R_2$ are, independently, hydrogen, alkyl, aralkyl, alkoxy, alkoxycarbonyl, amino or amino substituted with one or two alkyl, aralkyl or acyl groups, m and n are independently 1, 2 or 3; X is a bond between two carbons, an oxygen or sulphur atom, a group N—$R_3$ —in which the group $R_3$ has one of the meanings defined about for R—or an alkylene or alkenylene bridge containing from 1 to 5 carbon atoms and which may contain one or more substituents $R_4$—which are, respectively, hydrogen, lower alkyl, alkenyl or alkylidene having one to four carbon atoms with a linear or branched chain, phenyl, phenyl substituted with one or more lower alkyl groups having one to four carbon atoms, lower alkoxy groups having one to four carbon atoms or halogen groups, aralkyl, lower alkoxy containing from one to four carbon atoms, and hydroxyl—and when X is an alkenylene group, the latter may be fused to a saturated or unsaturated carbocyclic ring system, it being possible for the ring to be substituted with one or more groups $R_5$—which are lower alkyl or lower alkoxy having one to four carbon atoms, or halogen; Y is an alkenylene bridge containing from 3 to 5 carbon atoms and which may contain one or more substituents $R_4$ as defined above; and

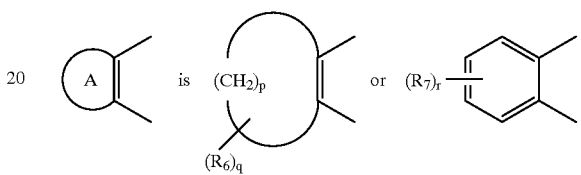

p being an integer which is 3 or 4, q being an integer from 1 to 3 inclusive, and r being an integer from 1 to 4 inclusive, and $R_6$ and $R_7$ being substituents which are individually hydrogen, halogen, lower alkoxy or lower alkyl.

2. Compounds according to claim 1, in which R is hydrogen.

3. Compounds according to claim 1, in which m and n are both equal to one.

4. Compounds according to claim 2, of general formula

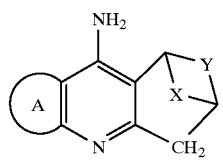

in which A, X and Y have the meanings stated in claim 1.

5. Compounds according to claim 1, in which

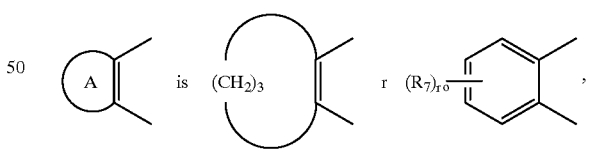

$R_7$ being hydrogen, halogen, or lower alkyl having 1 to 4 carbon atoms and r having the values 1 or 2.

6. Compounds according to claim 1, in which X is an ortho-phenylene group, a methylene group or a methylene group substituted with one or more groups $R_4$, it being possible for the said groups $R_4$ to be, independently, equal to lower alkyl, lower alkoxy, hydroxyl or, jointly, a lower alkylidene group.

7. Compounds according to claim 1, in which Y is an alkenylene bridge containing 3 carbon atoms, the central carbon of which can be substituted with a group $R_4$ which has the meaning stated in claim 1.

8. Compounds according to claim 4, of general formula

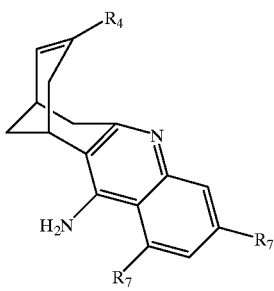

in which $R_4$ can be hydrogen, lower alkyl having 1 to 4 carbon atoms or phenyl, and $R_7$ can be hydrogen or halogen.

9. A pharmaceutical composition which comprises an effective acetylcholinesterase-inhibiting amount of at least one of the compounds of claim 1.

10. A process for obtaining polycyclic aminopyridine compounds of general Formula I

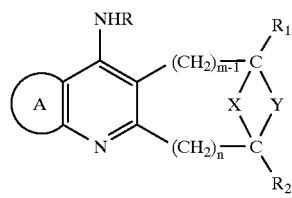 (I)

and their pharmaceutically acceptable salts, in which: R is hydrogen, alkyl, aralkyl, or acyl; $R_1$ and $R_2$ are, independently, hydrogen, alkyl, aralkyl, alkoxy, alkoxycarbonyl, amino or amino substituted with one or two alkyl, aralkyl or acyl groups; m and n are independently 1, 2 or 3; X is a bond between two carbons, an oxygen or sulphur atom, a group N—$R_3$—in which the group $R_3$ has one of the meanings defined about for R—or an alkylene or alkenylene bridge containing from 1 to 5 carbon atoms and which may contain one or more substituents $R_4$—which are, respectively, hydrogen, lower alkyl, alkenyl or alkylidene having one to four carbon atoms with a linear or branched chain, phenyl, phenyl substituted with one or more lower alkyl groups having one to four carbon atoms, lower alkoxy groups having one to four carbon atoms or halogen groups, aralkyl, lower alkoxy containing from one to four carbon atoms, and hydroxyl—and when X is an alkenylene group, the latter may be fused to a saturated or unsaturated carbocyclic ring system, it being possible for the ring to be substituted with one or more groups $R_5$—which are lower alkyl or lower alkoxy having one to four carbon atoms, or halogen; Y is an alkenylene bridge containing from 3 to 5 carbon atoms and which may contain one or more substituents $R_4$ as defined above; and

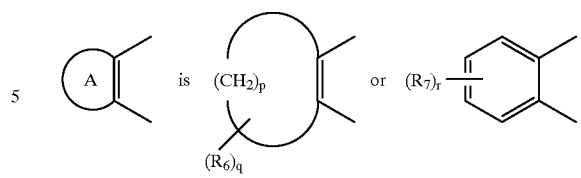

p being an integer which is 3 or 4, q being an integer from 1 to 3 inclusive, and r being integer from an 1 to 4 inclusive, and $R_6$ and $R_7$ being substituents which are individually hydrogen, halogen, lower alkoxy or lower alkyl, the said process wherein ketones of general Formula (11)

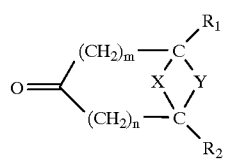 (II)

are reacted with the aminonitriles of general formula (III)

(III)

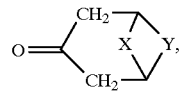

in which general formulae (II) and (III) A, $R_1$ and $R_2$, X, Y, m and n have the meanings defined above, and, if necessary, when it is desired to obtain compounds in which R is other than hydrogen, the compounds of general structure (I) in which R is hydrogen are subjected to alkylation, aralkylation or acylation; or, when it is desired to obtain compounds in which $R_4$ is an endo hydroxyl group, the corresponding keto precursor in which $R_4$ is an oxo group is subjected to reduction; thereafter, if so desired, to form a pharmaceutically acceptable acid addition salt, a basic compound obtained is reacted with a suitable acid.

11. A process according to claim 10, characterized in that the starting ketones (II) correspond to the general formula

in which X and Y have the meanings stated in claim 10.

12. A process according to claim 10, in which the reaction between the ketones (II) and the aminonitriles (III) is performed in the presence of a Lewis acid as catalyst or of a dehydrating agent.

13. A method of treating Alzheimer's disease by administering a compound of claim 1 to a subject suffering from said disease.

14. Compounds according to claim 8, wherein $R_7$ is fluorine or chlorine.

* * * * *